(12) United States Patent
Collins et al.

(10) Patent No.: US 12,364,989 B2
(45) Date of Patent: Jul. 22, 2025

(54) HIGH THROUGHPUT METHOD AND SYSTEM FOR ANALYZING THE EFFECTS OF AGENTS ON PLANARIA

(71) Applicants: Eva-Maria S. Collins, Wallingford, PA (US); Danielle Ireland, Highlands Ranch, CO (US); Siqi Zhang, San Diego, CA (US)

(72) Inventors: Eva-Maria S. Collins, Wallingford, PA (US); Danielle Ireland, Highlands Ranch, CO (US); Siqi Zhang, San Diego, CA (US)

(73) Assignee: INVERITEK, LLC, Wallingford, PA (US)

( * ) Notice: Subject to any disclaimer, the term of this patent is extended or adjusted under 35 U.S.C. 154(b) by 1844 days.

(21) Appl. No.: 16/237,959

(22) Filed: Jan. 2, 2019

(65) Prior Publication Data

US 2020/0209223 A1 Jul. 2, 2020

(51) Int. Cl.
| | |
|---|---|
| *B01L 9/00* | (2006.01) |
| *A61K 49/00* | (2006.01) |
| *B01L 3/00* | (2006.01) |
| *B01L 7/00* | (2006.01) |
| *G01N 33/50* | (2006.01) |
| *G01N 35/00* | (2006.01) |
| *G01N 35/02* | (2006.01) |
| *G06F 18/24* | (2023.01) |
| *G06T 7/00* | (2017.01) |
| *G06T 7/20* | (2017.01) |
| *G06V 10/764* | (2022.01) |
| *G06V 10/82* | (2022.01) |

(52) U.S. Cl.
CPC .......... *B01L 9/523* (2013.01); *A61K 49/0008* (2013.01); *B01L 3/5085* (2013.01); *B01L 3/545* (2013.01); *B01L 7/52* (2013.01); *G01N 33/5085* (2013.01); *G01N 35/00029* (2013.01); *G01N 35/00722* (2013.01); *G01N 35/00732* (2013.01); *G01N 35/02* (2013.01); *G06T 7/0012* (2013.01); *G06T 7/20* (2013.01); *G06V 10/764* (2022.01); *G06V 10/82* (2022.01); *B01L 2300/021* (2013.01); *B01L 2300/0609* (2013.01); *B01L 2300/1822* (2013.01); *G01N 2035/00158* (2013.01); *G01N 2035/00831* (2013.01); *G01N 2035/00841* (2013.01); *G01N 2035/00891* (2013.01); *G01N 2333/43526* (2013.01); *G06F 18/24* (2023.01); *G06T 2207/10004* (2013.01); *G06T 2207/10016* (2013.01); *G06T 2207/10152* (2013.01); *G06T 2207/30072* (2013.01)

(58) Field of Classification Search
CPC ........ B01L 9/523; B01L 3/5085; B01L 3/545; B01L 7/52; B01L 2300/021; B01L 2300/0609; B01L 2300/1822; B01L 2300/0829; A61K 49/0008; G01N 33/5085; G01N 35/00029; G01N 35/00722; G01N 35/00732; G01N 35/02; G01N 2035/00158; G01N 2035/00831; G01N 2035/00841; G01N 2035/00891; G01N 2333/43526; G01N 35/028; G01N 2035/0424; G01N 33/5097; G01N 2500/10; G06T 7/0012; G06T 7/20; G06T 2207/10004; G06T 2207/10016; G06T 2207/10152; G06T 2207/30072; G06V 10/764; G06V 10/82; G06F 18/24
See application file for complete search history.

(56) References Cited

U.S. PATENT DOCUMENTS 6,800,452 B1 * 10/2004 McNeil ........................ 435/29

OTHER PUBLICATIONS

Hagstrom D, Cochet-Escartin O, Collins EM. Planarian brain regeneration as a model system for developmental neurotoxicology. Regeneration (Oxf). Mar. 15, 2016;3(2):65-77. doi: 10.1002/reg2.52. PMID: 27499880; PMCID: PMC4895328. (Year: 2016).*
Blauch, Lucas R., et al. "Microfluidic guillotine for single-cell wound repair studies." Proceedings of the National Academy of Sciences 114.28 (2017): 7283-7288. (Year: 2017).*
Meldrum, Deirdre. "Automation for genomics, part one: preparation for sequencing." Genome research 10.8 (2000): 1081-1092. (Year: 2000).*
Hagstrom, "Freshwater Planarians as an Alternative Animal Model for Neurotoxicology", Toxicological Sciences, 147(1), 270-285, 2015.
Best and Morita: "Planarians as a Model System for In Vitro Teratogenesis Studies", Teratogenesis, Carcinogenesis, and Mutagenesis, 2:277-291, 1982.

(Continued)

*Primary Examiner* — Larry D Riggs, II
*Assistant Examiner* — Kettip Kriangchaivech
(74) *Attorney, Agent, or Firm* — MEAGHER EMANUEL LAKS GOLDBERG & LIAO, LLP

(57) ABSTRACT

A high throughput system and method for analyzing the effects of a plurality of agents on planaria is disclosed. Multiple test zones are provided, where each test zone contains at least a portion of one planarian. The planaria in each test zone are then exposed to at least one agent, the test zones are sealed, and at various times, the test zones are moved automatically between a storage location and at least one assay station. At each assay station, the test zones are exposed to a set of conditions, and an image or video of the planaria in the test zones are captured. Automated image or video analysis is used to are evaluate and determine whether the agent has an effect.

9 Claims, 13 Drawing Sheets

(56) References Cited

OTHER PUBLICATIONS

Inoue et al., "Thermosensory Signaling by TRPM Is Processed by Brain Serotonergic Neurons to Produce Planarian Thermotaxis", The Journal of Neuroscience, 34(47): 15701-15714, Nov. 19, 2014.
Inoue et al.: "Morphological and Functional Recovery of the Planarian Photosensing System during Head Regeneration", Zoological Science, 21: 275-283, 2004.
Birkholz and Beane: "The planarian TRPA1 homolog mediates extraocular behavioral responses to near-ultraviolet light", Journal of Experimental Biology,220, 2616-2625, 2017.
Paskin et al., "Planarian Phototactic Assay Reveals Differential Behavioral Responses Based on Wavelength", PLOS ONE, Dec. 10, 2014.
Zhang, et al, "Multi-Behavioral Endpoint Testing of an 87-Chemical Compound Library in Freshwater Planarians", Toxicological Sciences, 1-19, Jun. 8, 2018.
Zhang et al., "Effects of N,N-dimethylformamide on behaviour and regeneration of planarian Dugesia japonica", Toxicology and Industrial Health, 29(8), 753-760, 2012.

\* cited by examiner

HIGH THROUGHPUT METHOD AND SYSTEM FOR ANALYZING THE EFFECTS OF AGENTS ON PLANARIA

BACKGROUND

There is an increased recognition in the field of toxicology and pharmacology of the value of medium-to-high-throughput screening methods using in vitro and alternative animal models. Traditional toxicology testing has relied on low-throughput, expensive mammalian studies. Previous work has shown that the asexual freshwater planarian *Dugesia japonica* can function as a novel alternative animal model for neurotoxicology and developmental neurotoxicology. (See Hagstrom, Toxicological Sciences, 2015). However, the current methodologies do not cover the wide range of tests needed for toxicological studies, and the system does not scale for high throughput methodologies.

As such, a method and system capable of providing high throughput testing of planaria, with a broad range of available tests, is needed and desirable.

BRIEF SUMMARY

A high throughput method for analyzing the effects of a plurality of agents on planaria is disclosed. The method involves providing multiple test zones, where each test zone contains at least a portion of one planarian. The planaria in each test zone are then exposed to at least one agent and the test zones are sealed. The test zones are moved automatically between assay stations. At each assay station, the test zones are exposed to a set of conditions, and an image or video of the planaria in the test zones are captured. The intent of the stations is to assay different aspects of planaria regeneration/development, health, and behavior. The images or video are evaluated using computational methods to determine whether the agent has an effect, and the test zones are moved to another assay station.

Advantageously, the assay stations may each be one of the following assay stations: (i) an assay station configured to quantify stickiness by having the assay station generate a mechanical disturbance within a test zone, capturing images or video of the test zone, and evaluating the captured images or video using computational image analysis to determine when the at least a portion of one planarian detaches from a surface; (ii) an assay station configured to quantify body morphology, overall health, and/or fission rates by capturing images or video of a test zone and evaluating the captured images or video using computational image analysis to score physical body characteristics; (iii) an assay station configured to quantify chemotaxis by capturing images or video of a test zone and evaluating the captured images or video using computational image analysis to score behavior of each of at least one portion of one planarian in each of the test zones; (iv) an assay station configured to quantify vibriosensation by capturing images or video of a test zone and evaluating the captured images or video using computational image analysis to score behavior of each of at least one portion of one planarian in each of the test zones; (v) an assay station configured to quantify scrunching and/or noxious stimuli sensation by capturing images or video of a test zone and evaluating the captured images or video using computational image analysis to score behavior of each of at least one portion of one planarian in each of the test zones; (vi) an assay station configured to quantify temperature sensing, including creating a temperature gradient, capturing images or video of the test zone, and evaluating the captured images or video using computational image analysis to score behavior; (vii) an assay station configured to quantify light detection by exposing each test zone with light at different times, capturing at least one image of the test zone when exposed to a first light having at least a first peak wavelength and at least one image of the test zone when exposed to a second light having a second peak wavelength, and evaluating the captured images using computational image analysis to score behavior in response to the first and second lights; (viii) an assay station configured to quantify viability or lethality by capturing images or video of a test zone and evaluating the captured images or video using computational image analysis to classify each of at least one portion of one planarian in each of the test zones as alive or dead; (ix) an assay station configured to quantify regeneration by capturing an image of a test zone and evaluating the captured image using computational image analysis to quantify regeneration dynamics; and/or (x) an assay station configured to quantify unstimulated behavior/locomotion by capturing images or video of an unstimulated test zone and evaluating the captured images or video using computational image analysis to track at least one portion of one planarian over a period of between 30 seconds and 10 minutes.

Advantageously, images of each test zone may be captured beginning 15 minutes after the at least a portion of one planarian is added to the test zone and capturing at least one image on any (or every) day from day 1 through day 30 after the at least a portion of one planarian is added to the test zone.

In certain embodiments, each of the test zones may be a well in a multi-well array, and/or each of the test zones is marked with a unique identifying mark, and in certain embodiments, the unique identifying mark and data from each evaluation are stored in a database.

In certain embodiments, a planarian is amputated into two or more fragments using an automated guillotine. In certain embodiments, the at least a portion of one planarian is placed in the test zone using an automated planarian loading machine.

In certain embodiments, the method also includes evaluating whether the agent has any effect on a planarian's ability to integrate across multiple stimuli.

Also disclosed is a system for analyzing the effects of agents on planaria. The system includes multiple assay stations, each capable of being recorded by at least one camera. The system may include a variety of stations depending on the specific testing regime, including stations that are configured to test lethality, unstimulated behavior, locomotion, chemotaxis, phototaxis, thermotaxis, regeneration, scrunching, body morphology, general health, fission rates, generational studies, vibriosensation, and/or stickiness. The system uses a device such as a crane or plate handler (including robotic arms), or a conveyor belt to move multi-well arrays into and out of each assay station. The system also includes one or more processors and memory that control the movement of the multi-well arrays as well as the assay stations, receive and parses data from the cameras, and uses computational image analyses to evaluate the data.

Certain embodiments also include a planaria loading machine and/or an automated guillotine for decapitating planaria, configured to decapitate at least one planarian, instructions for reading an identifying mark on a multi-well array and associating that mark with data or analysis, and/or a display capable of displaying the analyses further comprising a display, wherein the at least one processor and memory further comprise machine readable instructions that, when executed, displays the analyses of the data to a user, and stores the data and analyses in a database.

Certain embodiments may utilize an assay station configured to generate a mechanical disturbance within one or more wells of a multi-well array, an assay station utilizing a plurality of peltier devices configured to expose each well to approximately the same temperature gradient, and/or an assay station utilizing a first light capable of irradiating a well of the multi-well array at a first point in time with radiation having a first peak wavelength and a second light capable of irradiating a well of the multi-well array at a second point in time with radiation having a second peak wavelength.

Also disclosed is a portable version of the system for analyzing the effects of agents on planaria. Depending on the specific testing regime, the system may include two or more stations configured to test lethality, unstimulated behavior, locomotion, chemotaxis, phototaxis, thermotaxis, regeneration, scrunching, body morphology, general health, fission rates, generational studies, vibriosensation, and/or stickiness. The system does not utilize cranes or plate handlers. The system also includes one or more processors and memory that control the assay stations, receive data from the cameras, and may also parse data or use computational image analyses to evaluate the data. In some embodiments, the data is transmitted to a remote server for analysis.

DETAILED DESCRIPTION

Figure 1:
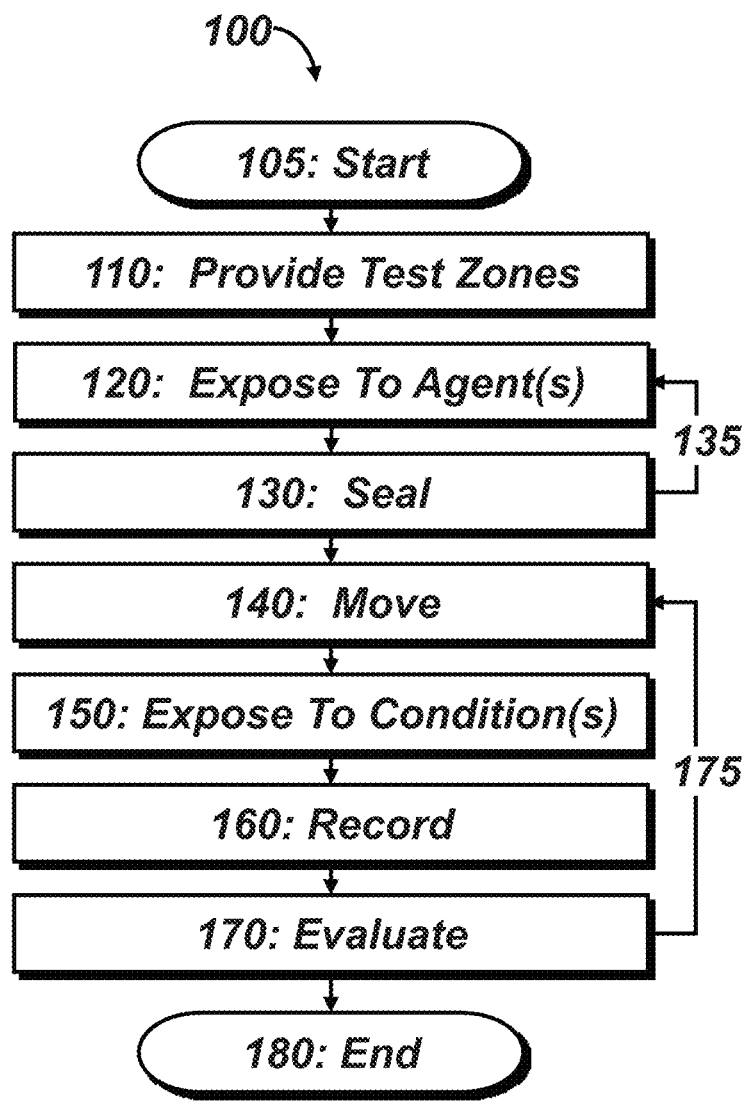
FIG. 1 is a flowchart describing an embodiment of the disclosed method.

As used herein, articles such as "a" and "an" when used in a claim, are understood to mean one or more of what is claimed or described.

As used herein, the expression "at least one" means one or more and thus includes individual components as well as mixtures/combinations. All percentages listed are by weight unless otherwise noted.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the terms "include", "includes" and "including" are meant to be non-limiting.

Disclosed is a high throughput system and method for analyzing the effects of a plurality of agents on planaria.

Because planarians can regenerate, this system and method has the unique advantage to allow for the study of both: (1) acute and chronic effects on the nervous system resulting from exposure of neuroactive agents and neurotoxicants, and (2) neuronal repair and/or regeneration after the agent(s) are removed from the planarians. The system thus has broad applicability in pharmacology, toxicology, and neuroregeneration research, as it enables studies of neuroefficacy, tolerance, and pharmacokinetic interactions among neuroactive drugs, withdrawal effects after removal of neuroactive compounds, as well as studies of neurotoxicity and developmental neurotoxicity of one or more agents, and the repair of such neuronal damage after agent removal.

The suitability of freshwater planarians for such synergy and withdrawal studies has been well documented, but existing studies have been limited in their throughput and range of tested behaviors as well as largely qualitative analyses. As neuronal subpopulations are regenerated, specific behavioral functions are restored, allowing researchers to differentiate between the effects of different agents on neuronal subpopulations. This unique opportunity provided by the planarian system was recognized as early as 1982 by Best and Morita (Best & Morita, *Teratogenesis, Carcinogenesis, and Mutagenesis* 1982) and has since been utilized to study the effects of several neurotoxicants, including ethanol and Dimethyl sulfoxide (DMSO). However, as with studies on adult worms, these behavioral tests have been limited in their throughput and range of behaviors tested, primarily relying on planarian locomotor velocity (pLMV) and phototaxis.

Importantly, behavioral tests can be conducted in parallel on both regenerating and intact animals allowing determination of development-specific efficacy or toxicity. For example, this type of comparison has led to demonstrations of the increased sensitivity of regenerating planarians to DMSO and ethanol. Certain embodiments use multiple time points, as developmental toxicity could be manifested as either the complete loss of a behavior or just delayed reacquisition.

In summary, automated behavioral testing allows for time and cost-efficient screening of neuronal efficacy or potential impairment of neuronal function before investigating the underlying mechanisms. Because the specific neurotransmitters and pathways involved in some of these behaviors have been determined (Inoue et al., *The Journal of Neuroscience* 2004; Inoue et al., *Zoological Letters* 2015), characterizing behavioral effects upon neuroactive drug or neurotoxicant exposure can serve as a starting point for in-depth analysis of the responsible molecular mechanisms. Furthermore, behavioral profiling of known agents can be used to classify new compounds whose mechanism is not yet known.

Referring to FIG. 1, the method (100) begins (105) by providing multiple test zones (110). Although any chemically compatible test zone is acceptable, in certain embodiments, each test zone is a well in a multi-well array (or plate). Preferred plates have 6, 12, 24, 48, or 96 wells.

Preferably, each plate has an identifying mark associated with the plate. For example, each plate could have an ID number marked in a specific corner and/or along an edge.

Other approaches include, but are not limited to, 1-D or 2-D barcodes, such as Code 128, Code 39, UPC, Data Matrix, PDF417, or QR codes. These identifying marks can be used as aids for positioning and orientation of the plates, or for tracking the plates (such as knowing which plate was screened by what assay at what time, etc.). These marks may be read by a scanner at a given assay station or at any other location used by the system.

Each test zone should have at least a portion of one planarian. Adults, developing, and/or regenerating planaria may be used in certain embodiments. Certain embodiments may use freshwater planaria. Preferably, species such as *Dugesia japonica* are used. When not used for screening, planarians may be stored in 1× planarian water which may be Montjuic salts (IVIS) (Cebria and Newmark, Development 2005) or Instant Ocean (TO) water in, e.g., plastic containers at 20° C. in a refrigerated incubator in the dark or in specialized tanks/aquaria in a temperature and light-controlled room. Animals may be fed, e.g., organic chicken or beef liver once a week and cleaned twice a week when not used for experiments (Dunkel et al., *Physical Biology* 2011). Test animals may be randomly selected from a healthy population. Fully regenerated worms which had not been fed within at least one week and which were found gliding normally in the container may be used. Worms may be selected that fall within a certain range of sizes. For example, in some embodiments, worms may have a mean length of between 3 and 4 mm, with standard deviations up to 1 mm. Automated size measurement may be utilized.

Although freshwater planaria of the species *Dugesia japonica* or *Schmidtea mediterranea* are preferred, other planaria, including land and marine planaria, including related species of a similar size, can also be used.

Figure 2:
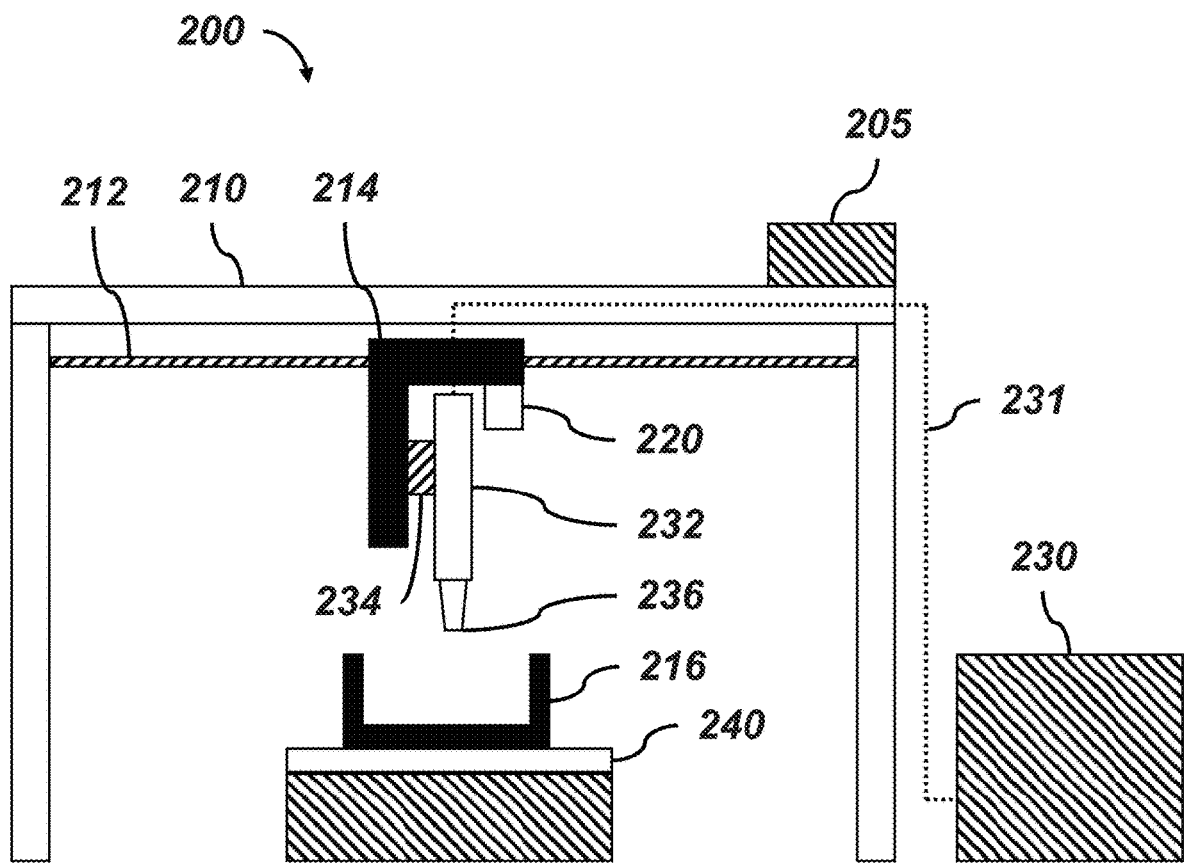
FIG. 2 is a diagrammatic illustration of an automated loader.

Planaria may be loaded manually into the test zones/wells or using an automated loading device as illustrated in FIG. 2. Certain embodiments of the automated loader (200) may comprise or consist of a computer-controlled robot able to locate individual planarians in a storage container, extract them, and transfer them into a well. The system (200) may be controlled by, e.g., a Raspberry Pi microcontroller (205) and may consist of at least three subsystems. The three subsystems are configured to allow the pickup of the planarian by, e.g., a pipettor, the transfer of the planarian into a well, and then the release of the planarian.

The first subsystem is a motorized frame (210), controlled by at least one microprocessor, such as the processor on a Raspberry Pi, providing a X-Y cartesian gantry (212) for moving a platform (214) into positions above the wells (216) and/or storage locations. The X-Y cartesian gantry (212) may include linear actuators, motors connected to a worm gear, or other approaches known in the art. In certain embodiments, the motorized frame may be constructed from steel and aluminum and driven by stepper motors. The second subsystem is the visualization subsystem that allows the system to identify planarians in a particular location. This may be a camera (220), controlled by a microprocessor (205) and operably connected to the moving platform (214), and allows for real-time monitoring of the planarians in the storage area or wells and object-based tracking to identify a planarian, e.g., through the use of image processing software such as OpenCV. The third subsystem is the suction system, for collecting and holding the planarians while moving. The pickup and release of the planarian may be regulated by, e.g., a pneumatic pump, which may also be computer-controlled by, e.g., the Raspberry Pi microcontroller and used to apply a specific amount of suction, which was empirically determined to minimize tissue damage to each planarian. This subsystem may include a pump (230), including pneumatic pumps such as a peristaltic pump, controlled by a microprocessor (205) and operably connected (231) to a pipettor (232). The pipettor may be operably connected to the moving platform (214). The platform may contain other microprocessor-controlled motors or actuators (234) that are configured to move at least the pipettor in the z-direction (in FIG. 2, closer or further from well (216)). In certain embodiments, the entire moving platform may be controlled to move in the z-direction. The system can thus move the tip (236) of the pipettor (232) in any x-y-z direction, in order pick up a planarian that was previously identified by the image analysis software.

Because planarians can adhere to a substrate, in certain embodiments the system may also include, e.g., a vortex shaker (240), to dislodge planarians before object recognition occurs.

Figure 3:
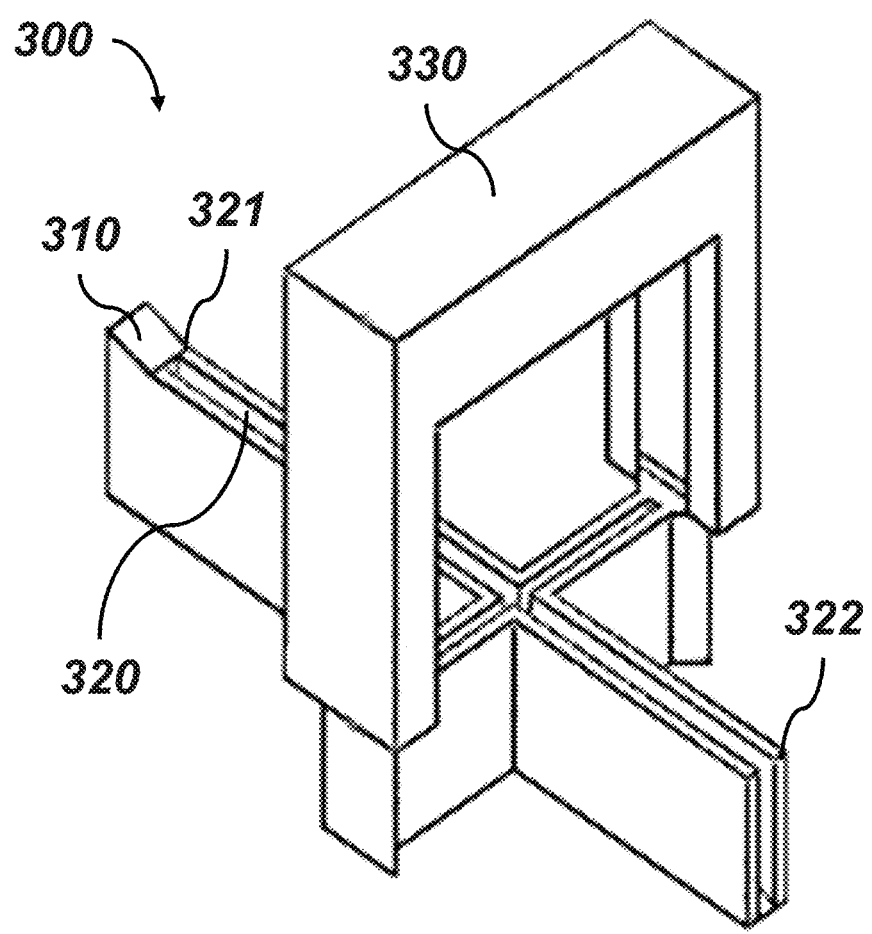
FIG. 3 is a diagrammatic illustration of an automated guillotine.

When only a portion of a planarian is desired, an automated guillotine, such as the one illustrated in FIG. 3, may be used to cut a planarian. Referring to FIG. 3, certain embodiments of the device (300) use gravitationally-driven flow to propagate the planaria in a narrow channel at a desired spacing to enable serial amputation in the guillotine. At least one planaria is added to a start reservoir filled preferably with planarian water. A slope (310) is used to drive the fluid from a start reservoir (not shown) down a narrow channel (320) to the guillotine (330). The slope (310) may begin before the start (321) of the channel (320) and may continue some or all of the way towards the end (322) of the channel (320). At least one of the planaria then moves in the direction of the flow. The flow can be adjusted by adjusting the slope (310) and thus the spacing between planaria and the speed with which the planaria move can be controlled. In certain embodiments, the slope is fixed. In certain embodiments, the slope may be controlled or adjusted at any time. In certain embodiments, the planaria reaching the guillotine is detected by a light gate consisting of a laser diode and a photodetector (not shown), which will activate the guillotine to drop down and amputate the planaria. In certain embodiments the guillotine consists of a 22×22 mm plastic cover slip and is controlled by two servo motors with gears (not shown), which translate the rotational motion of the servos into linear motion and are automatically controlled by a control board and computer. The amputated pieces can then be collected, and the guillotine be set back to its start position for the next amputation. When used in conjunction with an automated loader, the loader can be configured to pick a planarian and place it in a start reservoir or at the start of the narrow channel, have the planarian run through the automated guillotine, then the automated loader can be used afterwards to identify a head or tail piece and place one or both of those into a test zone/well.

Once the desired planaria have been added to each test zone, test zones are exposed to one or more agents (120). In some embodiments, one test zone is used as a control, such as an agent-free control. In some embodiments, multiple test zones are used as controls. In some embodiments, both positive and negative controls are used.

In some embodiments, each test zone is exposed to a different agent. In other embodiments, multiple test zones are exposed to the same agent, including different concentrations of the same agent. In other embodiments, one or multiple wells are exposed to more than one agent. For example, in one embodiment, using a 6-well plate, five wells were exposed to a single agent and one well was kept agent-free.

Once the test zones have been exposed to agent(s), each test zone is preferably sealed (130) to prevent transport in or out of each test zone. Often, this is simply a matter of applying a lid (with or without additional parafilm sealing) or an adhesive transparent polymer film.

In some embodiments, multiple plates are initially prepared. Although not required, one embodiment provides several multi-well plates (110), then repeats (135) the process of exposing the wells in each plate to agent(s) (120) and sealing them (130) until all of the provided plates are sealed. Solutions may be exchanged daily, only on certain days, or not at all.

After sealing, the test zones may be moved (140) to an assay station or be stored in the dark while not screened. Each assay station is designed to expose the test zone to a particular set of conditions (150), capturing an image or video of the planarian in each of the test zones (160), and evaluating whether the agent has at least one measurable effect (170) on the tested animals. In some embodiments, the evaluation (170) is done, and then the sequence of moving-exposing-recording-evaluation is repeated (175). In other embodiments, after the recording step (160), the test zones are moved to another station, and the evaluation occurs while the test zones are moved-exposed-and-recorded at another assay station. In other embodiments, the evaluations are done after all assay stations are completed. In some embodiments, the evaluations are done remotely. For example, in some embodiments, the recordings are saved to a remote server, and the server then handles the evaluation.

In certain embodiments, images or video of a test zone are captured beginning 15 minutes after a portion of one planarian is added to a test zone. In certain embodiments, images or video are captured on at least one day from day 1 through day 30 after a portion of one planarian is added to a test zone. Thus, in certain embodiments, an image or video could be captured 15 minutes after a planarian is added to a test zone to provide a "starting point", and then additional images and/or video could be recorded on day 1, day 5, and day 15 of the tests.

In certain embodiments, the test stations are moved to an assay station on a defined schedule over a period of up to 30 days, preferably up to 15 days, more preferably up to 12 days, and still more preferably up to 10 days. In certain embodiments, each test zone is assayed by all stations on 2 days of the defined periods, such as days 7 and 12, or days 6 or 7 and 10. In other embodiments, the assays are performed on 3 days of the defined periods, such as day 2, 8, and 15. In certain embodiments, the assays are performed every day.

For each assay station, each individual portion of one planarian in the multi-well plate is imaged by at least one camera. In some embodiments, one camera is configured to capture all wells. In other embodiments, multiple cameras work together to capture all of the wells. For example, with a 48 well plate arranged in an 6×8 array, the system can be configured to use 12 cameras, each configured to capture 4 wells in a 2×2 arrangement. Alternatively, the system could use 6 cameras, each configured to record 9 wells in a 3×3 arrangement, with the last pair of cameras only actually recording 6 wells each. In other embodiments, a camera is assigned to capture a single well. These cameras capture either images or video of the wells, which are then analyzed.

Lethality.

This assay is typically used to screen the effects of an agent on planarian health and regeneration. During preparation of the plates, certain approaches are typically taken when lethality is to be tested, where each test zone contains either a full planarian or a previously amputated animal. In some embodiments, half of the wells in each row of a multi-well plate contain a full animal, and half contain a previously amputated animal. In certain embodiments, each plate includes either full animals or previously amputated animals. In preferred embodiments, the previously amputated animal had been amputated within 3 hours of being placed in the well and the agent being added.

In certain embodiments, screening plates may be prepared. In certain embodiments, the wells may initially contain 200 µL of water, then a small amount, such as 20 µL, of the planarian water may be removed and a small dose, such as 20 µL, of an appropriate chemical solution containing an agent at a particular concentration is added to each well. In other embodiments, the wells may contain only, e.g., 180 µL of water and 20 µL of a chemical may then be added (no water is removed). In one example, a Tecan printer is used to dispense very small volumes; only about 1 µL of a chemical, or enough DMSO to normalize the DMSO concentration, is added to each well containing 200 µL of planarian water. For each concentration of a chemical, at least two independent experiments with 8 full planarians and 8 regenerating planarians may be performed as biological replicates, thus at least 16 full and regenerating animals would be assayed for each condition.

After preparing the plates, animals may be stored in the plate at room temperature in the dark. At desired points in time, including but not limited to every day, every other day, or days 2, 4, 8, and 15 following application of the agent, the plates are removed from storage and one or more cameras are used to record images or video of each well. Preferably, agitation of each test zone may be applied before images are recorded to activate the planarians to move.

Image processing and machine learning (ML) techniques may then be used to automate processing of the images or video. The ML techniques may include supervised, unsupervised, and reinforcement learning techniques. The ML algorithms may include, but are not limited to linear regression, logistic regression, decision tree, SVM, naïve Bayes, KNN, k-means, random forest, dimensionality reduction algorithms, or gradient boosting algorithms.

Figure 10A:
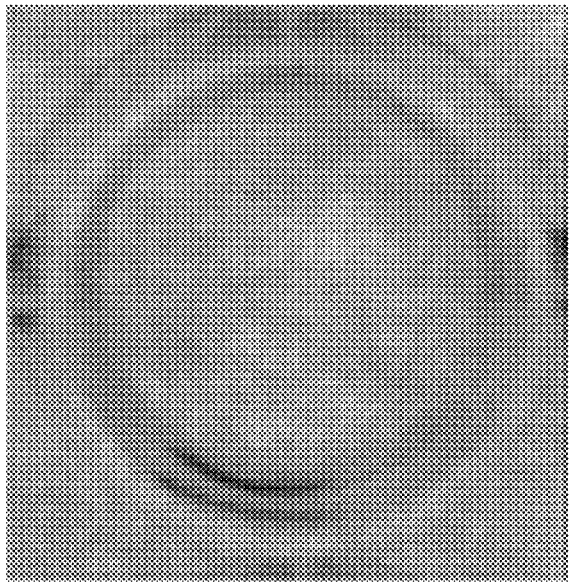
FIGS. 10A-10B are images illustrating image processing for a single well.
Figure 10B:
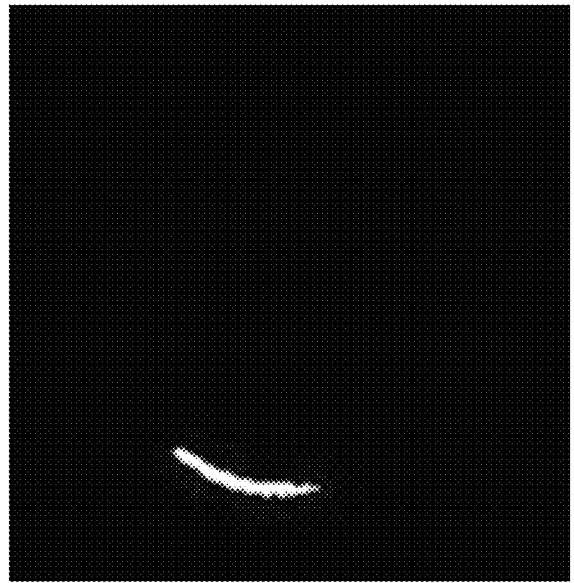
Figure 10C:
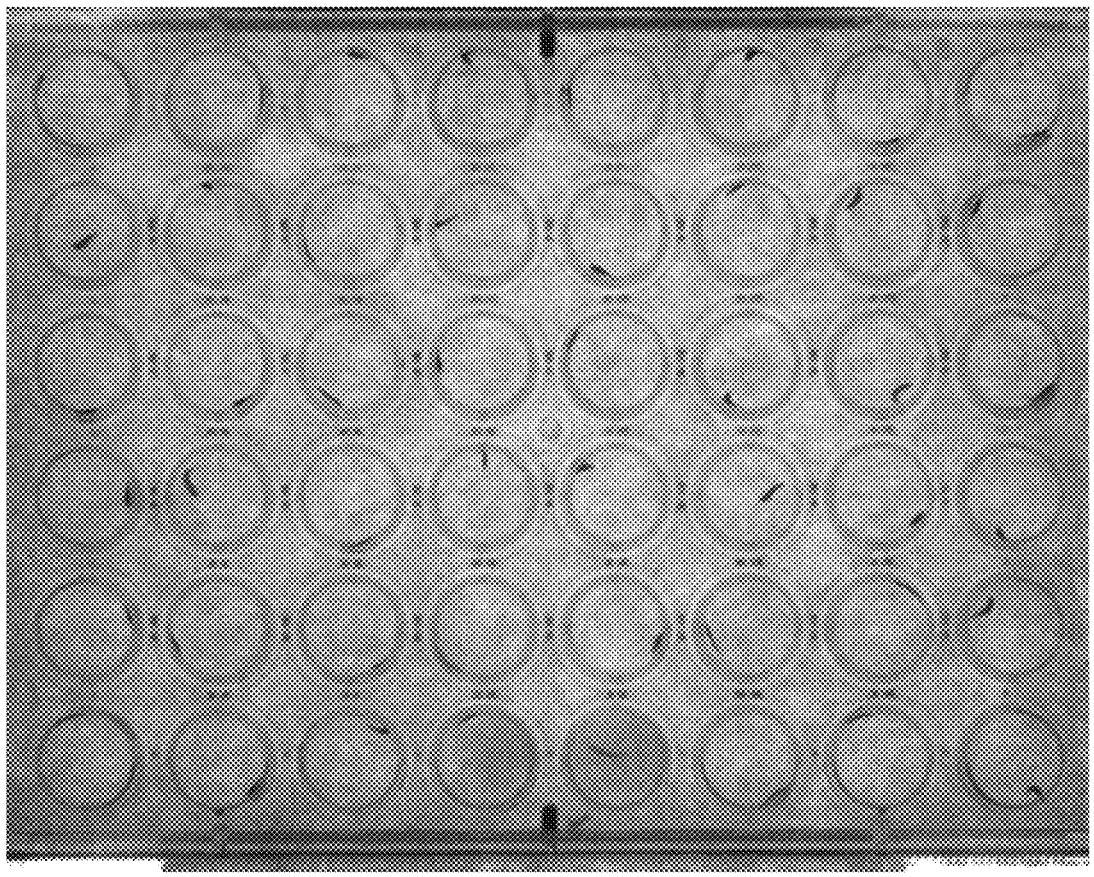
FIGS. 10C-10D are images illustrating image processing for a 48-well array.
Figure 10D:
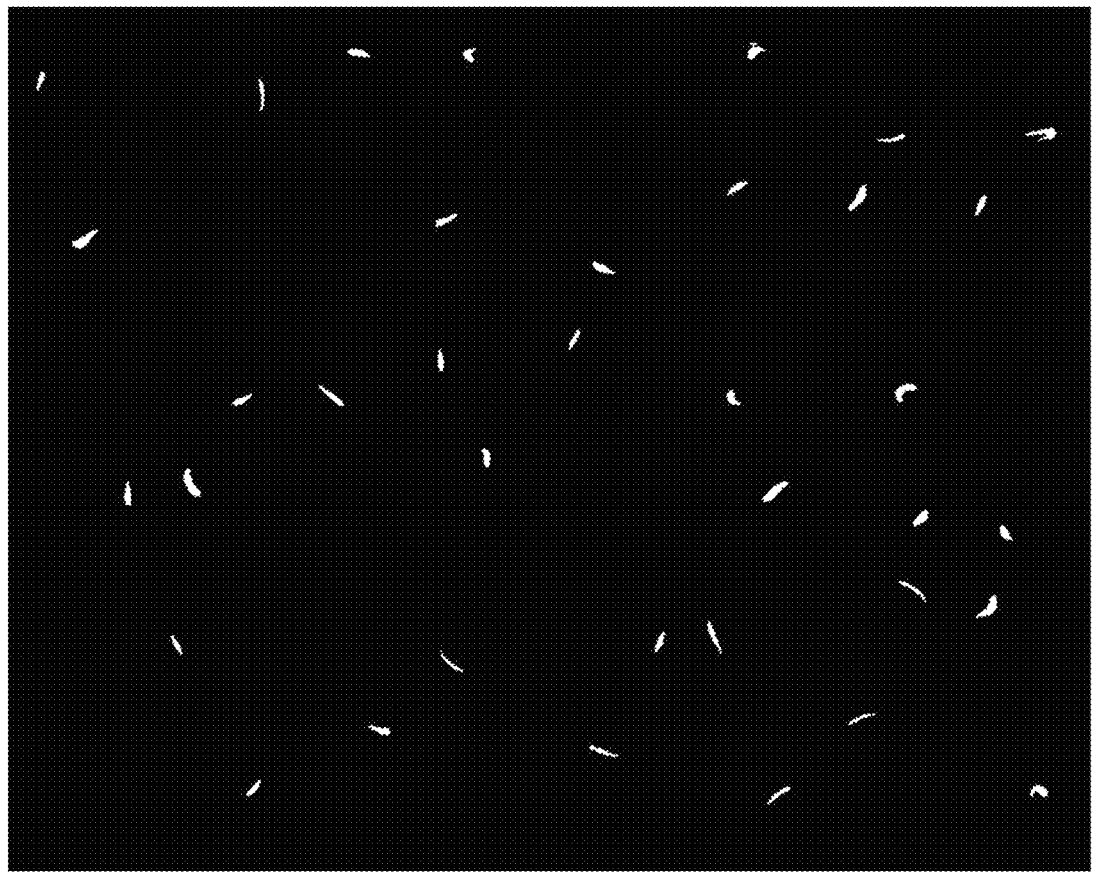

In particular embodiments, incoming images are cropped into images of individual test zones, each image is then corrected for background, converted to grayscale if not already using grayscale images, blurred slightly, thresholded to produce a binarized image, and then the contours are found. FIGS. 10A and 10B depict images of a single well. FIG. 10A shows a grayscale image of a single well. FIG. 10B shows the same image after processing. FIGS. 10C and 10D depict images of a 48-well array. FIG. 10C shows a grayscale image of the array, while FIG. 10D shows the same array after image processing.

A trained algorithm can be used to compare the contours of an image from a first point in time to contours of one or more images at a later point in time. In some embodiments, between 1 and 5 seconds, between 1 and 10 seconds, between 1 and 20 seconds, or between 1 and 30 seconds of video are captured, and multiple frames from that video are analyzed, up to and including having every frame analyzed. In some instances, the system is designed to capture a certain number of frames—up to 20, up to 50, up to 100, or up to 250 frames—rather than capture for a set period of time. The trained algorithm can then discriminate live animals from dead animals based on the degree of change in the contours.

The fraction of dead worms may be plotted and fitted using (Selderslaghs et al., 2009):

$$y = \left( \frac{1}{1 + 10^{(\log LC_{50} - x) \times Hill\,slope}} \right)$$

with y the fraction of dead individuals, x the logarithm of the chemical concentration to obtain the $LC_{50}$ and Hill slope is the slope factor of the dose-response curve. In some embodiments, the two asymptotes of the original Hill equation may be forced to be 0 and 1.

Body Morphology.

Figure 4A:
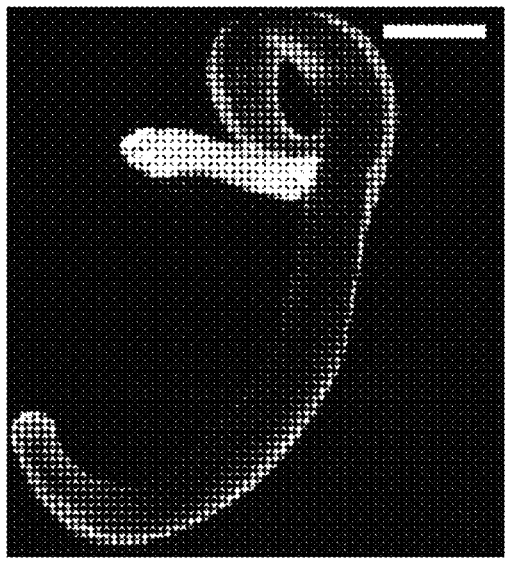
FIGS. 4A-4E are images illustrating various shapes a planarian can assume.
Figure 4B:
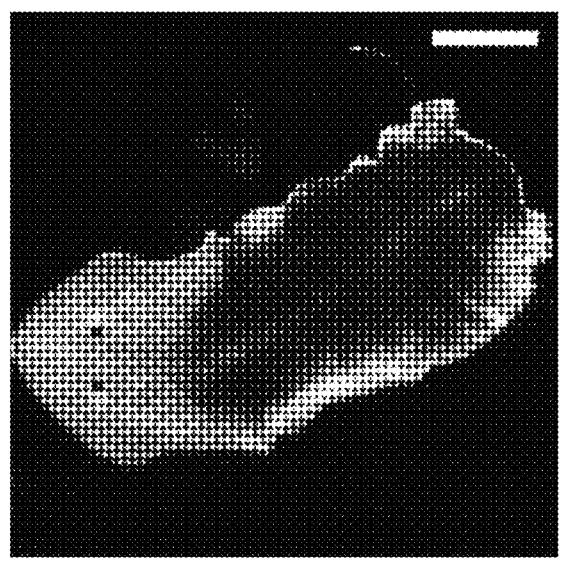
Figure 4C:
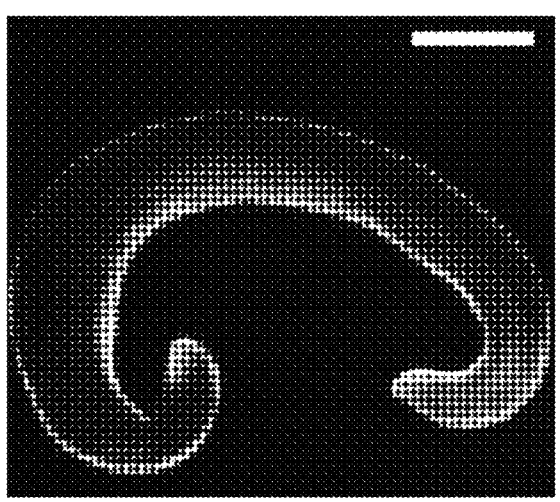
Figure 4D:
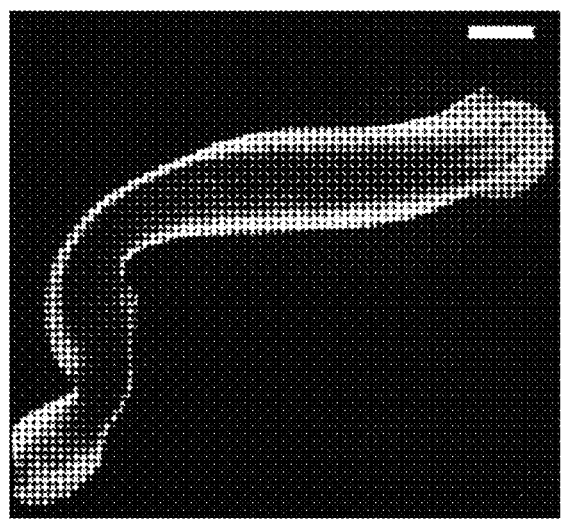
Figure 4E:
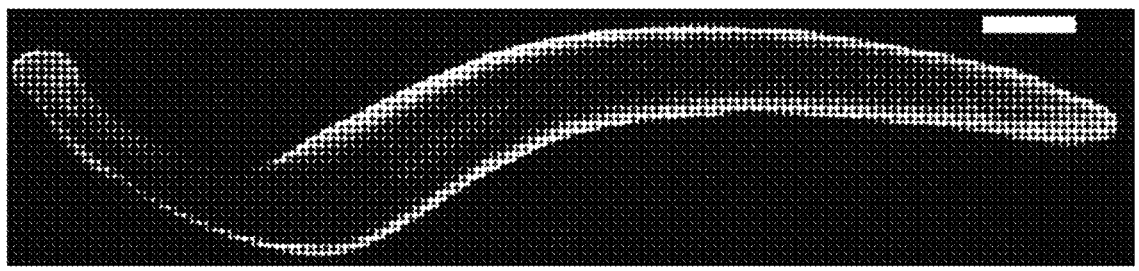

This assay is used to screen the effects of an agent on planarian body morphology. In this assay, each individual portion of a planarian in the multi-well plate is imaged by at least one camera. In some embodiments, one camera is configured to capture all wells. In other embodiments, multiple cameras work together to capture all of the wells. For example, with a 48 well plate arranged in an 6×8 array, the system can be configured to use 12 cameras, each configured to capture 4 wells in a 2×2 arrangement. Alternatively, the system could use 6 cameras, each configured to record 9 wells in a 3×3 arrangement, with the last pair of cameras only actually recording 6 wells each. Alternatively, the system could use 4 cameras to scan the 48-well plate to capture images of each single well, or a single camera to capture all wells. In other embodiments, a camera is assigned to capture a single well. These cameras capture either images or video of the wells, which are then analyzed. Image processing and machine learning (ML) techniques may then be used to automate processing of the images or video. In particular embodiments, incoming images are cropped into images of individual test zones, each image is then converted to grayscale, blurred slightly, thresholded to produce a binarized image, and then the contours are found. Once the contours are found, the contours can be run through a trained ML algorithm to score stereotypical planarian morphologies, which includes but is not limited to those seen in FIGS. 4A-4E, which includes pharynx protrusions (FIG. 4A), contractions (FIG. 4B), C-shape hyperkinesia (FIG. 4C), screw-like hyperkinesia (FIG. 4D) and snake-like motion (FIG. 4E). Body morphologies may be static or dynamic, i.e., change over time and include multiple different morphologies for a single planaria. Body morphologies can thus also be used as behavioral descriptors. In certain embodiments shape changes over time are used to measure induction of seizures and snake-like locomotion.

In one embodiment, for each agent concentration tested, screening plates may be prepared as described in the lethality section.

Unstimulated and Locomotive Behavior.

These assays are typically used to measure the gliding speed of individual planarians and determine the percent of time spent in a given locomotive type: resting, swimming, or gliding. In certain embodiments, images or video are recorded for a period ranging from 30 seconds to 10 minutes, and preferably between 30 seconds and 6 minutes, and more preferably between 1 minutes and 4 minutes. In certain embodiments, agitation, such as with a vortex shaker, may be applied before images are recorded.

In preferred embodiments, a red backlight is used to aid imaging.

Image processing and machine learning (ML) techniques may then be used to automate processing of the images or video. In particular embodiments, incoming images are cropped into images of individual test zones, each image is then corrected for background, converted to grayscale, blurred slightly, thresholded to produce a binarized image, and then the contours are found. Further image processing, such as area filters, may be applied to retain actual worms and discard noise.

Figure 11:
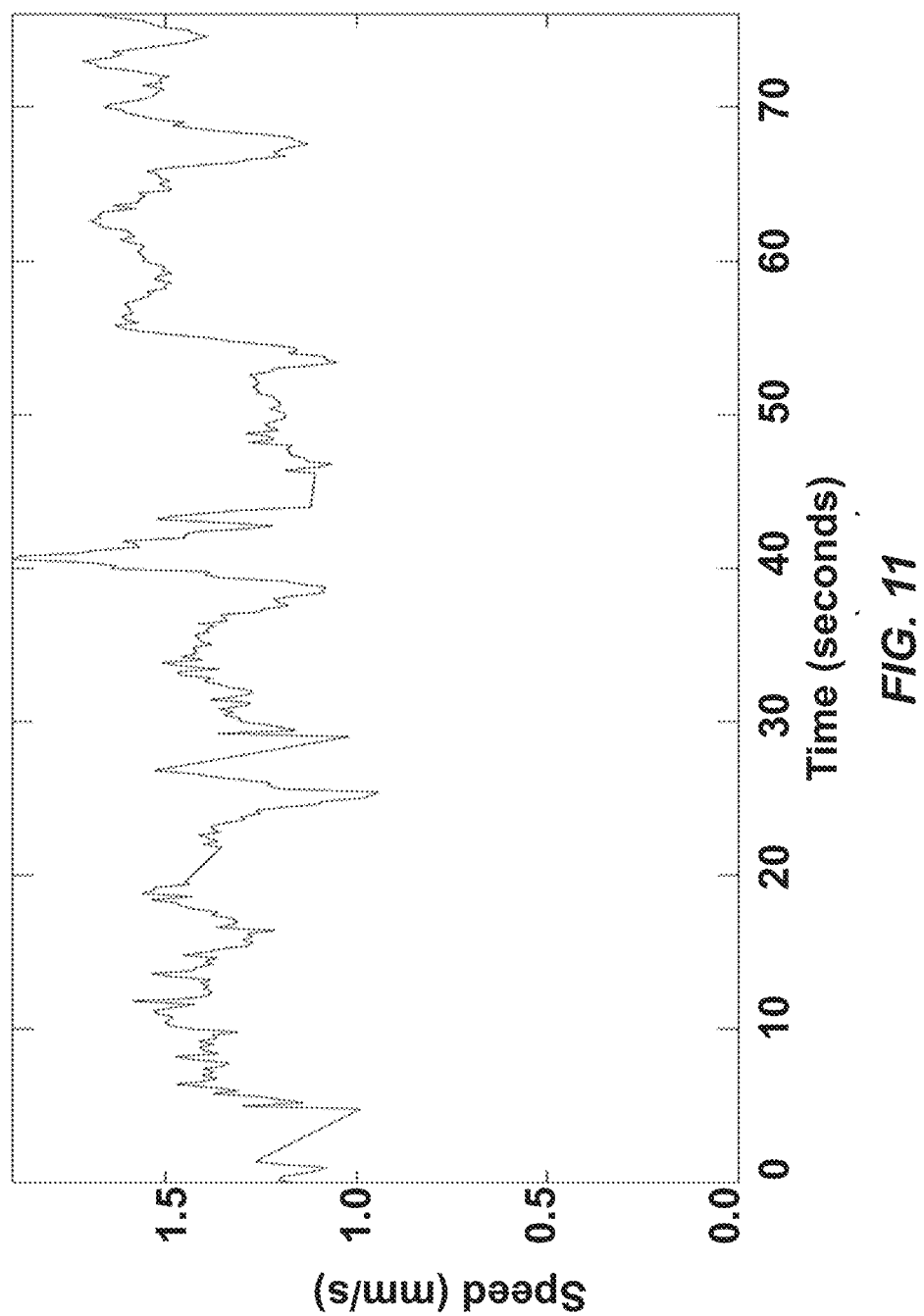
FIG. 11 is a graph illustrating speed over time for a monitored planarian.

A trained algorithm can be used to compare the contours of an image from a first point in time to contours of one or more images at a later point in time. In some embodiments, between 1 and 5 minutes of video are captured for each test zone, and every frame is analyzed. In this fashion, the position of each worm at each desired time point may be detected. In certain embodiments, the center of mass (COM) of each worm is estimated and tracked over a period of time. The trajectory of the worm may then be reconstructed from these tracked positions, which can be used to calculate worm speeds and/or total distance travelled. The speeds for one or more animals may be captured for a period of time; as shown in FIG. 11, the speed of a single planarian was tracked at approximately 5 frames per second (fps) over a period of 75 seconds, and the speed in mm/s at each point was graphed. It should be noted that some data points are missing; in some embodiments, the speed is not measured for every frame. In some embodiments, when the position of the worm cannot be accurately detected, the system ignores the speed calculation for that frame.

In certain embodiments, speed histograms may be computed and fit to a double Gaussian function. The first (slowest) Gaussian corresponds to worms swimming while the second corresponds to gliding. Based on these histograms, three behaviors may be defined: resting, swimming, and gliding for the entire population. Alternately, an algorithm may be trained to discriminate these behaviors without requiring histogram computation and fitting to Gaussian functions. The fraction of time spent in each behavior may be recorded for each worm separately.

In certain embodiments, a dynamic profile may also be generated from this data. Because the acquired data may be COM tracking over time, in addition to determining a single value for average speed by time averaging all the data, one can generate a comparison of a profile of control worm instantaneous speeds to the instantaneous speed profile of an exposed worm. In cases where the exposed worm profile falls outside a threshold number of standard deviations (e.g., 2 or 3, etc.) of the control worm profile for specific time periods, this can be considered an effect. In some embodiments, the dynamic profile is graphed over time. In some embodiments, the dynamic profile is converted into a binary code of fixed length intervals where 1 denotes an effect and 0 denotes no effect for that specific time interval. These binary codes can then be compared across agents to delineate which agents evoke similar binary codes and thus behavioral profiles.

In one embodiment, for each agent concentration tested, screening plates may be prepared as described in the lethality section.

As planarians tend to rest when stored in the dark, screening plates may firstly be shaken for, e.g., 6 s at 900 rpm on a microplate shaker (which may also be used in other assays, such as the lethality assay), to encourage motion before imaging. The screening plate may then be moved by the automatic plate handler onto a transparent plate holder. There it may be imaged for, e.g., 3 min at, e.g. 5 fps, by a single camera, with a cold LED panel (B&H Photo Video, New York, New York) equipped with a red filter (Roscolux) placed under the transparent plate holder to provide illumination for tracking.

In some embodiments, image acquisition may be controlled through a custom script, such as a LabVIEW (National Instruments) script.

In a certain example embodiment, image analysis was performed using a custom MATLAB script, based on COM tracking. An average intensity projection image was first generated from the entire movie and subtracted from each picture in the stack. The resulting images were thresholded to obtain the planarian's outline and each planarian was automatically assigned a well number while its center of mass, length, and area were recorded. This assay may provide two readouts: (i) the fraction of time spent resting and (ii) the instantaneous speed of locomotion. The instantaneous speeds may be calculated for all tracks over a short interval, e.g., 2-s intervals, to increase the signal-to-noise ratio. An empirically determined absolute speed cutoff may be used to distinguish the planarians' moving and resting behaviors. In this one example, instantaneous speeds <0.5 mm/s were considered to represent resting and were disregarded in speed calculations. The fraction of time spent resting was calculated as the amount of time resting divided by the total time tracked. Speed values >0.5 mm/s represent planarian locomotion and were averaged to calculate the mean speed for each planarian. Of note, this speed includes instances of both swimming and gliding. Planarians with no tracking data (i.e., tracking was lost for worms moving at the edge of the well due to low contrast) may be considered non-analyzable and excluded from further analysis. In one example, in <4% of day 7 plates and <12% of day 12 plates (full animal and regenerating tails), 1 or 2 animals were non-analyzable. In one example, in approximately 1% of the day 12 plates, 3-5 animals were excluded. To accurately determine the COM of each planarian, the tracking analysis may be specifically optimized for fissioned worms, i.e., planarians which have split into two pieces (head and tail) as part of their normal asexual reproduction. For fissioned worms, when the head and tail pieces are distinguishable, analysis may only be performed on the head piece. In other embodiments, when the head and tail pieces are indistinguishable, analysis may only be performed on the fastest piece, as heads generally move faster.

In another example, gliding, swimming and resting behaviors were distinguished based on speed. A speed below 0.3 mm/s was considered as the planarian's resting or wiggling speed. To distinguish swimming from gliding, a dynamic cutoff was defined as follows: the speed distribution of the entire population of 24 worms was computed and fitted by the sum of two Gaussians and a constant value according to:

$$a_1 e^{\frac{-(x-\mu_1)^2}{\sigma_1^2}} + a_2 e^{\frac{-(x-\mu_2)^2}{\sigma_2^2}} + c$$

The fit was performed using the built-in MATLAB fit function and nonlinear least square method. The fit output was shown graphically on top of the raw data. In case of poor fit results, the user may manually determine the relevant parameters instead.

Planarians were considered as gliding at any time point for which the speed was larger than $\mu_2 - 1.5\sigma_2$, a value that was adapted by hand to represent the behavior of control populations. The worms were declared swimming at time points for which the speed was between the absolute resting cutoff and this dynamic gliding cutoff.

From this population level classification, each planarian was assigned a fraction of time spent in each of the three behaviors for all time points tracked. To remove bias due to differences in worm size, the animal's speed was scaled by its aspect ratio, calculated as the ratio of the planarian's length squared to the area, $l^2/lw$ or $l^2/A$, to reduce noise in the measurement. Based on control populations and the MATLAB built-in power law fit tool, the gliding speed scaled with the power ⅔ of this aspect ratio. Thus, in some embodiments, a scaled gliding speed may be defined as the absolute gliding speed divided by that measurement. All measurements may be averaged over the entire population and error bars may be calculated as the standard error of the mean. Of note, the contribution of each planarian to the mean may not be weighed by the time for which it was tracked, thus treating all worms equal. In some embodiments, the dynamic speed profiles may be used and agent-treated planarians be compared to control planarians in their behavior over time, similar to the approach described above for unstimulated behavior.

In other embodiments, as exampled above with respect to unstimulated behavior, only two behaviors—(i) resting and (ii) gliding and swimming are differentiated, which simplifies the calculations and training required accordingly.

Similarly, in certain embodiments, speed may not be scaled by the planarian's aspect ratio. While for full planarians gliding speed is roughly proportional to a planarian's aspect ratio, this is not true for heads from recently fissioned worms. A head piece can move at a similar speed to the original parent worm, i.e. the speeds of unfissioned tails at day 7 and head pieces resulting from fissions of regenerating tails move with comparable speeds, while differing substantially in their aspect ratio. Thus, for fissioned heads, scaling by aspect ratio is not appropriate. In addition, as measurement may be largely affected by the planarian's shape and location in the well, the automated measurement of aspect ratio may be challenging, and so absolute movement speed may also be used in certain embodiments.

Chemotaxis.

This assay is typically used to detect the planarian's ability to sense food or spatially localized chemical attractants. A small volume of chemicals mixed with agarose, or food, either mixed with agarose or not, is injected to the center of each well by a multi-pipette. While this injection may be done manually, it may also be automated and/or computer controlled, using either commercial liquid dispenser or custom-built solutions. In other embodiments, a transparent pipet tip containing the chemical and/or food is added to the well by inserting the pipet tip into the well. No agarose or injection is used; the pipet merely stays in position and the presence of the food in the pipet is sensed by the planarians.

In the absence of food, planarians show a tendency of swimming at the edge of the well. However, in the presence of food or a chemical stimulus in the well center, worms will move to the center of the well if capable of chemotaxis. After food or chemical stimulus has been provided, images of each well can be recorded. In preferred embodiments, images are recorded beginning immediately after the food or chemical stimulus has been provided. In other embodiments, images begin recording within 1 minute of the food being provided.

The images may be recorded as described for the unstimulated behavior assay. In certain embodiments, the area in the well is segmented to an area nearest to the food source, an area intermediate surrounding the food source, and an area far away from the food source. By comparing the amount of time worms spend in those areas individually, the response of worms to food or chemical stimulus can be quantified. The time it takes worms to react can also be quantified. In certain embodiments, various image processing techniques, such as standard deviation projections made using, e.g., ImageJ or MATLAB, allow the visualization of the areas where the worms spent the most time. In certain embodiments, the positioning of the food or chemical stimulus is known ahead of time and the locations categorized as being near or away from the food or chemical stimulus. In other embodiments, the location of the food or chemical stimulus introduction is captured by video or image, and the zone locations are automatically estimated based on cross sectional area of the well and the positioning of the food or chemical stimulus. Each image, or each frame of a video may then be processed to determine the location of the planaria in the well, and categorizing it as being near or far from the food or chemical stimulus. A trained algorithm can discriminate and score how long each planaria exists within each of the zones.

In one example, chemotaxis experiments were conducted in a standard 100 mm petri dish. The dish was filled with 25 ml MS prior to transferring 10-11 planarians. The liver mixture was prepared with organic chicken liver diluted by 1×MS at the ratio of 1:2. Each dish was imaged on a white LED panel by a Basler A641f camera at 5 fps. The dish was first imaged without any food for 10 min as a control for imaging. After the control imaging, 50 µL liver mixture was injected into the center of the dish slowly with a 200 µL pipet and the dish was imaged for 10 min. Image analysis was performed in MATLAB to track the movements of the planarians. A food area—a circle with half of the radius of the dish—was pre-defined for each group and applied to both videos with and without food. The amount of time worms spent in the food area during the second half of the videos with and without food, was calculated and compared with each other.

In another embodiment, for each agent concentration tested, screening plates may be prepared as described in the lethality section.

Phototaxis.

This assay is typically used to detect the planarians' response to light. Planarians are intrinsically photophobic and thus will react to bright light of certain wavelengths. In certain embodiments, one or more blue light pulses (typically having a peak wavelength between 450 and 495 nm) are applied in the assay as stimuli. Imaging is solely achieved by the red background light; the blue light is not seen by the camera as a long pass filter removes it.

Planaria detection is achieved in the same way as in the unstimulated behavior assay. In some embodiments, the characteristic planarian response to a blue light stimulus—to contract and wiggle its head within a few seconds—may be taken into account. In these embodiments, ML shape analysis is thus applied for that time frame and each worm is scored depending on its response or lack of response to light. In other embodiments, the average speed may be considered, similar to how it is handled for the unstimulated behavior assay.

In certain embodiments, a dynamic profile may also be generated from these data. Because the acquired data may be COM tracking over time, in addition to determining a single value for average speed by time averaging all the data, one can generate a comparison of a profile of control worm speeds to the speed profile of an exposed worm. In cases where the exposed worm speed profile falls outside of a threshold number of standard deviations (e.g., 2 or 3, etc.) of the control worm speed profile for specific time periods, this can be considered an effect. In some embodiments, the dynamic profile is graphed over time. In some embodiments the dynamic profile is converted into a binary code of fixed length intervals where 1 denotes an effect and 0 denotes no effect for that specific time interval. These binary codes can then be compared across agents to delineate which agents evoke similar binary codes and thus behavioral profiles.

In certain embodiments, one or more green light pulses (typically having a peak wavelength between 495 and 570 nm) are also applied, and similar recording and analysis may be utilized. Since planarians can detect blue light, but not green, with pigment in the skin (Birkholz and Beane, 2017; Paskin et al., 2014), the sensitivity of the phototaxis assay can be improved by utilizing a combination of blue and green light stimuli to distinguish specific photoreceptor defects (inability to respond to green light) from general defects in light sensing (inability to respond to both wavelengths of light).

One example can be described as follows. First, to lower the variability of the animals' background activity, the plate was placed onto the phototaxis station 4 minutes prior to the assay, allowing the planarians in the plate to acclimate. After 4 minutes, the plate was imaged for 5 minutes: 1-min red light acclimation ($1^{st}$ dark cycle), 1-min green light stimulation (light cycle), 2-min red light acclimation ($2^{nd}$ dark cycle), 1-min blue light stimulation (light cycle). Of note, the second dark cycle was 2 minutes to allow the planarians to acclimate and settle before the blue light stimulation, but only the activity in the last minute in the $2^{nd}$ dark cycle was analyzed. The average speed in each 1-min dark and light cycle was quantified as in the unstimulated and locomotive behavior assay and in (Zhang, et. al, *Toxicological Sciences* 2018). However, the phototactic response was quantified by calculating the difference of the average speed in each light cycle to that in the preceding dark cycle:

$$\Delta_{green\ light} = \text{average speed}_{green\ light\ cycle} - \text{average speed}_{1st\ dark\ cycle}$$

$$\Delta_{blue\ light} = \text{average speed}_{blue\ light\ cycle} - \text{average speed}_{2nd\ dark\ cycle}$$

Dead planarians were discarded from the analysis.

In one embodiment, for each agent concentration tested, screening plates may be prepared as described in the lethality section.

Thermotaxis.

This assay is typically used to detect a worm's response to a temperature gradient. Planarians prefer cold regions over warm regions. In this assay, each well of the plate is placed above a Peltier device configured to create a temperature gradient within each well. Preferably, the assay station is configured such that each test zone has a "cold" region (e.g., a corner or portion of the well) with a substantially identical temperature (+/−4 degrees C.), and a "warm" region with a substantially identical temperature, where the warm regions are not noxious heat, and each well is exposed to a similar temperature gradient. Following a period of cooling, or during the period of cooling, images may be recorded. In certain embodiments, the recording begins at least 2 minutes after cooling first begins.

The images may be recorded as described for the unstimulated and locomotive behavior assay. These may be quantified by comparing the amount of time spent in the cold and warm regions of the wells. In certain embodiments, various image processing techniques, such as standard deviation projections made using, e.g., ImageJ, allow the visualization of the areas where the worms spent the most time. In other embodiments, the temperature of each location in a well is known ahead of time and the locations categorized as being warm or cold. Each image, or each frame of a video is then processed to determine the location of the planaria, or at least the center of mass, within each test zone, and categorizing it as being in a cold zone or warm zone. A trained algorithm can discriminate and score how well each planaria stays within the cold zone or moves towards the cold zone.

In certain embodiments, a dynamic profile may also be generated from the data. For example, in addition to determining single values for how much time was spent in a cold or warm region, data could be captured over time that would allow the comparison of a profile of times from a control worm to the profile of times of an exposed worm. In cases where the exposed planarian's speed and location profile falls outside a threshold number of standard deviations (e.g., 2 or 3, etc.) of the control worm speed and location profile for specific time periods, this can be considered an effect. In some embodiments, the dynamic profile is graphed over time. In some embodiments the dynamic profile is converted into a binary code of fixed length intervals where 1 denotes an effect and 0 denotes no effect for that specific time interval. These binary codes can then be compared across agents to delineate which agents evoke similar binary codes and thus behavioral profiles.

Figure 8:
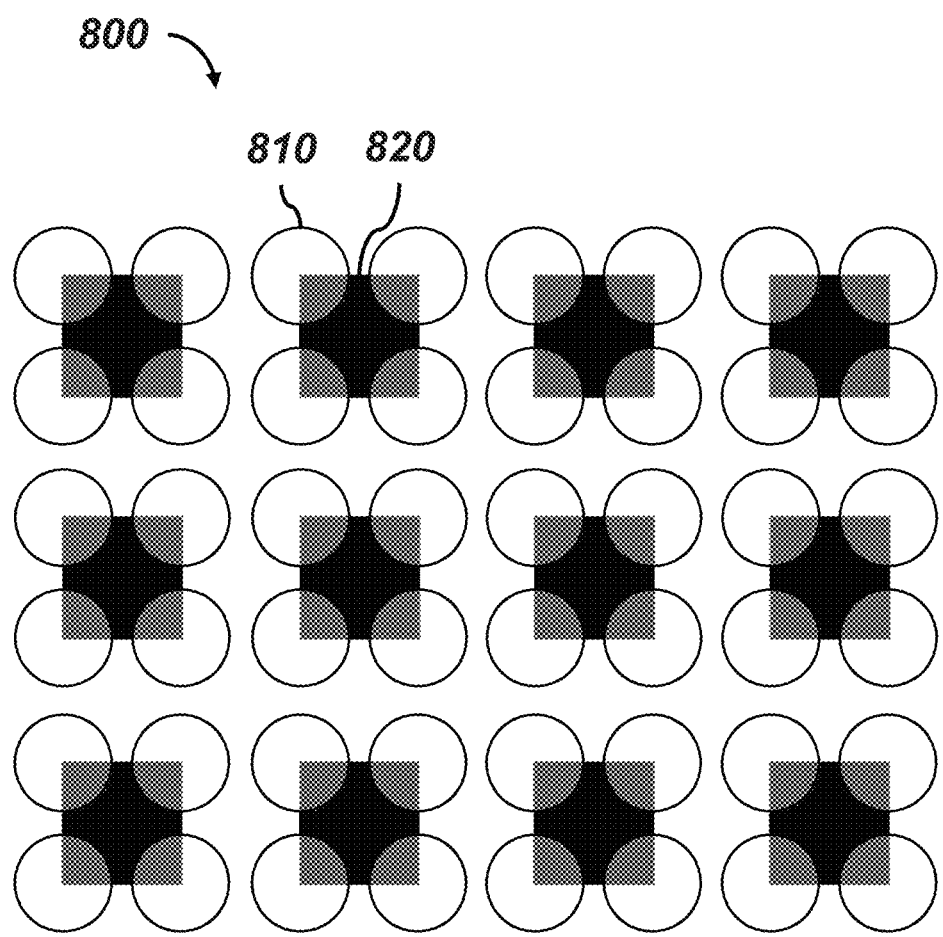
FIG. 8 is a diagrammatic illustration of an embodiment of an arrangement of peltier devices in a thermotaxis assay.

Referring to FIG. 8, in an example embodiment, a 48-well plate was placed on a custom setup with 12 peltiers (15 mm×15 mm) (Digi-key, Thief River Falls, MN) that were evenly spaced and embedded in an aluminum heat sink. The peltiers (820) were arranged in a matrix of 3 rows×4 columns (i.e. 4 wells (810) share one peltier) and powered by an AC to DC power supply (Amazon). This setup, which was controlled automatically through an Arduino board, created an identical heat gradient with a temperature difference of 3-4° C. in each well of the screening plate. During the assay, the plate was imaged without the heat gradient (ambient temperature) for 2 minutes, and then imaged with the heat gradient for 4 minutes by the single camera. The plate was illuminated from the top by a custom-made red LED ceiling light which does not obscure the view of the camera.

In this example embodiment, image analysis was performed using a custom, automated MATLAB script. The center of mass (COM) of each planarian was tracked over time and used to calculate the fraction of time the animal spent in the cold area in the well when the gradient is on. Since it takes time to establish a stable heat gradient across the well, only the fraction of time the planarian spent in the cold area during the last two minutes of the assay was accounted for. The cold area in each well was defined as the area of a sector with central angle of 120°.

In certain embodiments, the fraction of time the head piece spent in the cold area may be used.

Regeneration.

Figure 5:
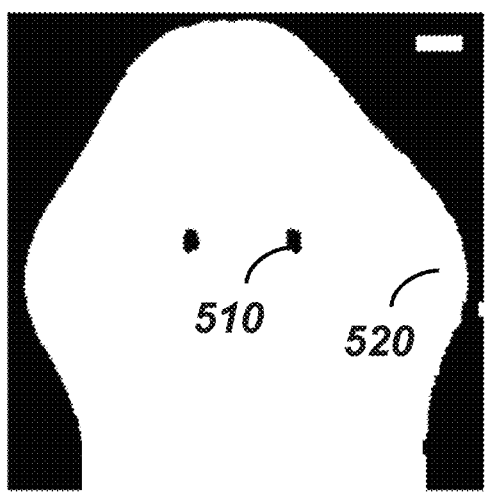
FIG. 5 is an image illustrating parts of a planarian that can be examined during regeneration assays.

This assay is typically used to characterize regeneration of the planaria. As is understood in the art, and in reference to FIG. 5, the general concept consists of scoring the reappearance of head structures such as the eye spots (510) or auricles (520), which typically reappear within 4-5 and 9 days of regeneration, respectively, in untreated animals.

Thus, a trained ML algorithm can receive images, process the images to focus on the head structure, eliminate speckles, eliminate background, and eliminate groups of dark pixels that are too large to be eye spots. In doing so, it can allow the algorithm to discriminate the appearance of head structures in the image and score the image based on the appearance of those structures. For example, the appearance of one eye but not both, or the appearance of eyes but not auricles.

In an example embodiment, image analysis was performed with a custom Python-based machine learning algorithm using a transfer learning neural network. A custom pre-processing program was used in Python to images of a planarian's head region from the original images. The cropped images were imported into the neural network, which categorized the worms based on a prediction of the number of eyes in the images: normal (2 eyes), abnormal (0, 1 eye or >2 eyes), and indeterminate (for example, when the worm was on the edge of the well, flipped over, or the head region was not properly cropped). The neural network was trained using a training set consisting of 2206 images of normal eyes, 1047 images of abnormal eyes and 6703 images with undetectable quality. The training set was labeled semi-manually with a customized computer program. The prediction results of each image for each alive planarian were integrated using a custom MATLAB script to make the final decision of the number of eyes in this regenerating animal. If more than 1 image frame predicted normal eyes, the planarian was determined to have normal eyes. If more than 1 image frame predicted abnormal eyes, but no image frame predicted normal eyes, the worm was determined to have abnormal eyes. In all other cases, the planarian was an "indeterminate" case, and discarded in the following analysis. Since the prediction of the "abnormal" category was often inaccurate because of the small training set and large variability in data, all results predicted to be "abnormal" and "indeterminate" were manually double checked. Of note, for planarians which underwent fission during the course of the screen, resulting in more than 1 animal in a well, the number of regenerated eyes in the head piece was scored manually. The eye regeneration rate was calculated as:

$$\text{eye regeneration rate} = \frac{\text{number of planarians with 2 eyes regenerated}}{\text{number of analyzable planarians}}$$

Comparison of different morphological endpoints provides increased sensitivity as certain chemicals may affect the regeneration of one structure but not the other, as evidenced by the effect of N,N-dimethylformamide on auricle but not eye regeneration (Zhang et al., *Toxicological and Industrial Health* 2013). Auricles, however, are not equally striking in all planarian species, with *D. dorotocephala* and *D. tigrina* being the most apparent and *S. mediterranea* the least (Carter et al., *Journal of Statistical Physics* 2015), limiting the applicability of this particular readout.

High-resolution light microscopy, or a camera having a sufficiently high resolution, may be used to quantify the rate of blastema growth during regeneration. Because the blastema is unpigmented, it can easily be distinguished from the rest of the pigmented worm body, allowing for automated image analysis. However, since different sized worms may have different regeneration rates, the size of the blastema must be normalized by worm size. Preferably, normalizing by the square of the worm's width should be used to account for size variation. Blastema growth rate is best used as an indicator of general developmental toxicology since it is not specific to neurodevelopmental defects per se. For example, in one experiment, a neurotoxic pesticide, permethrin, did not affect blastema growth rate, although it did delay eye reappearance (Hagstrom et al., *Toxicological Sciences* 2015).

Scrunching.

Figure 6:
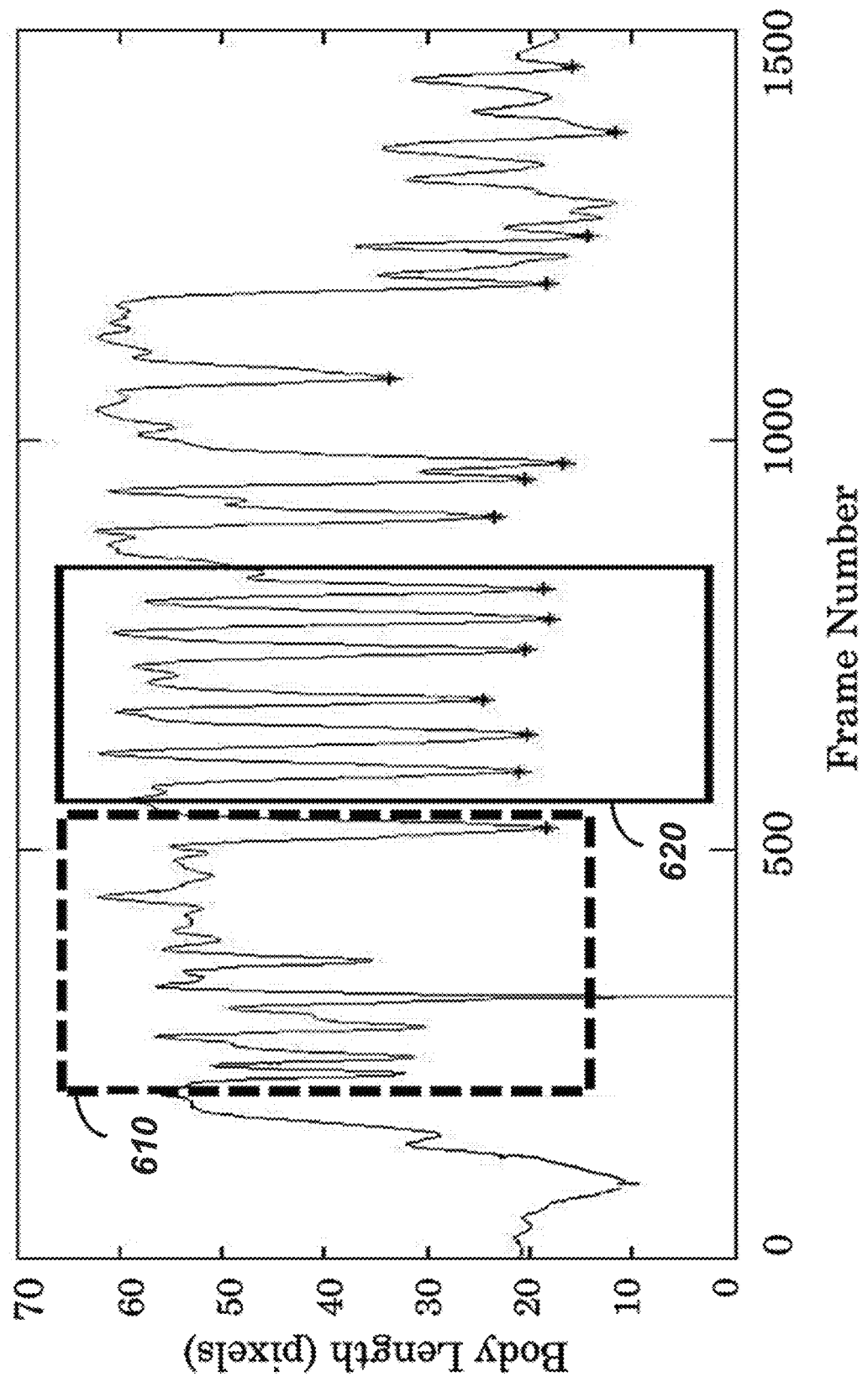
FIG. 6 is a graph illustrating body movements indicative of scrunching.

This assay is typically used to assay the planarians' ability to sense and react to noxious stimuli. Scrunching is the planarians' characteristic response to noxious stimuli and requires stimulus sensing, proper neuro-muscular communication, mucus secretion, and muscle function. Scrunching may be triggered by noxious heat. In some embodiments, a multi-well plate is heated from below by a Peltier component. Scrunching is detected by tracking the body length of the worm over time. A frequency of body length change over time can be used as the characteristic of scrunching in the analysis. As shown in FIG. 6, there may be periods where the body length changes do not have any particular frequency (610), and periods where there is a specific frequency (620). It is those periods where there is a specific frequency (620) that scrunching is indicated. A trained algorithm can be used to discriminate these features in conjunction with image analysis techniques. In some instances, the length of the animal is normalized prior to analyzing for scrunching. In some embodiments, these measurements may be used to quantify the reaction time—that is, how long it takes the animal to sense the noxious stimuli.

In one embodiment, for each agent concentration tested, screening plates may be prepared as described in the lethality section.

In one embodiment, to induce scrunching, the screening plate was placed on a peltier plate (TE Technology Inc., Traverse City, MI), which was controlled by the computer through a temperature controller board (TE Technology Inc.), to increase the aquatic temperature in the wells. The temperature of the peltier plate was initially set to 65° C. for the first 30 seconds to quickly heat up the plate from room temperature. Then, the temperature was gradually decreased to 43° C. to stabilize the aquatic temperature across the plate at around 32° C. for 4 minutes, which was sufficient to induce wild-type *D. japonica* to scrunch. The plate was imaged by the single camera and illuminated from above by a custom red LED ceiling light which does not obscure the view of the camera.

In one embodiment, image analysis of scrunching worms was performed using a custom, automated MATLAB script. The COM and length of each planarian were tracked over time. The worm's length over time was plotted and smoothed to detect instances of scrunching. Body length oscillations in the smoothed plot which fulfilled the scrunching criteria (asymmetric cycles, characteristic frequency) were extracted to determine instances of scrunching (see FIG. 6). Such oscillations consisting of >3 consecutive peaks in the body length versus time plot were defined as scrunching. If the planarian was dead or not properly detected (not enough tracking data), it was excluded. The automated image analysis was not possible with fissioned planarians and thus these animals were scored manually. Scrunching rate was calculated as:

$$\text{scrunching rate} = \frac{\text{total number of scrunching worms}}{\text{total number of analyzable worms}}.$$

Stickiness.

This assay is typically used to determine how strongly a planaria sticks to a substrate. Planarians secrete mucus for self-defense and locomotion, the latter of which is accomplished by cilia beating in a layer of secreted adhesive mucus. Increased mucus secretion or changes in mucus composition in response to environmental stimuli can increase mucus production and the worm's adhesion to its substrate ("stickiness"). Thus, stickiness assays can be used to determine the impact of an agent on a worm's mucus secretions.

The stickiness of planarians may be determined based on the worms' ability to adhere to a substrate given a mechanical disturbance to the environment, including vibrations, flow rate of a fluid in an animal's local environment, direct force measurement, etc.

In certain embodiments, images or video are captured as described above for unstimulated and locomotive behavior assays. The images may then be processed to allow the shape, position, direction of movement, and/or center of mass of the animal to be determined. Trained algorithms may be used to discriminate, e.g., typical and atypical motion patterns to determine when an animal has detached from a surface. For example, an animal that is moving in a first direction at 1 mm/s suddenly moves in a perpendicular direction at 5 mm/s, has likely been detached.

In one embodiment, a microplate orbital shaker (Big Bear Automation, Santa Clara, CA) was used to create controlled water flow to unstick the planarians from the bottom of the plate well. Different rotation speeds for full planarians and regenerating tails at day 7 and 12 were chosen based on preliminary testing to achieve a reproducible majority fraction of wild-type planarians to unstick. This intermediate unsticking capacity was chosen to be able to detect both an increase or decrease in planarian "stickiness". Day 7 for regenerating tails was observed as the relatively stickiest time-point, potentially due to locally increased secretion of mucus since the worms are less motile during regeneration. At day 7, the full planarian plates were shaken for 3 seconds at 552 revolutions per minute (rpm) and the regenerating tail plates for 3 seconds at 1017 rpm. Based on preliminary testing, full planarians kept in the screening plates for 12 days required greater water flow to be unstuck. Therefore at day 12, both full and regenerating tail plates, which are now more like adult animals, were shaken for 3 seconds at 665 rpm. The plate was imaged from above by a USB3 camera (FLIR Systems Inc., Wilsonville, OR) mounted on a ring stand and imaged at 8 fps. Each worm was manually scored as either "unstuck" (defined as being displaced by the water flow and floating in the well) or "stuck" (defined as worms which did not float during the whole plate shaking session). The fraction of unstuck planarians was calculated as:

$$\text{Fraction of unstuck planarians} = \frac{\text{the number of unstuck planarians}}{\text{the number of alive planarians}}$$

Fission Rates.

This assay is typically used to determine the impact of an agent on the spontaneous rate of fission (asexual reproduction by physical tearing of the body into a head and a tail piece) of a planarian. Image processing techniques can be used as described previously to identify body morphologies, but the algorithms can be trained to discriminate individual animals. In some embodiments, the fission rate is based on the number of wells on a plate that contain more than one object as a function of time. In some embodiments, this is measured at regular periods (every other day, every third day, etc.), while in other embodiments, this may simply be tested on an assigned schedule, including but not limited to being tested on days 1, 7, and 10. In some embodiments, the length of the animal may be used in determining fission and/or the fission rate. For example, if a single animal is 2 cm on day 1, and 1 cm on day 2, fission may have occurred, although this approach also captures instances of non-fission events, such as head regression.

In some embodiments, the image processing can be used to identify waist formation in a single planarian that occurs ahead of the separation into two animals (see Malinowski et al., *Proceedings of the National Academy of Sciences* 2017).

In certain embodiments, an image is captured on or before day 2, and additional images are captured at least once every 30 days, preferably at least once every 15 days, and still more preferably at least once every 5 days.

It should be noted that multiple objects in a single test zone (such as what results from a fission) may cause problems for some center of mass tracking algorithms. It should be recognized that any analysis that assumes a single object per test zone may not be accurate when multiple animals are present in a single test zone. In these instances, one option is to ensure the tracking algorithm is capable of handling fissioned (or multiple) worms. In one embodiment, tracks of the fissioned head and tail piece were distinguished by the speed of each piece, since the tail piece usually moves slower, and the slower piece was ignored. In other embodiments, both objects may be tracked and the results may be averaged.

General Health.

This assay is typically used to classify how many animals are healthy. This assay may be incorporated/integrated into the body morphology assay, or it may be assayed separately. The method is very similar to that for assaying body morphology, however, instead of classifying shapes, it is used to identify whether the planarians were healthy. The classifier in this case would be trained to identify features of unhealthy planarians, which may include but are not limited to lesions (identified as white regions on an otherwise brownish pigmented body), wrinkled body edges, or being headless. These may allow the ML algorithm to provide a health score (e.g., a 0 to 100 score), or to simply provide a binary determination of health or unhealthy.

Generational Studies.

This is typically used to determine how a treatment impacts later generations. The beginning of these studies may be incorporated and/or integrated into the fission rate assay, or it may be handled separately. In some embodiments, head and tail pieces are distinguished. As noted above, in some embodiments, tracks of the fissioned head and tail piece may be distinguished by the speed of each piece, since the tail piece usually moves slower. In one embodiment, the test examines the impact of an agent on the second generation (the tail resulting from a fission of a previously regenerated tail) animal in one or more of the other assays used by the system or method. In other embodiments, the parent animals are exposed to the agent first, and after fissioning or amputation, examining the impact on the offspring without exposing the offspring themselves.

Vibriosensation.

Figure 9:
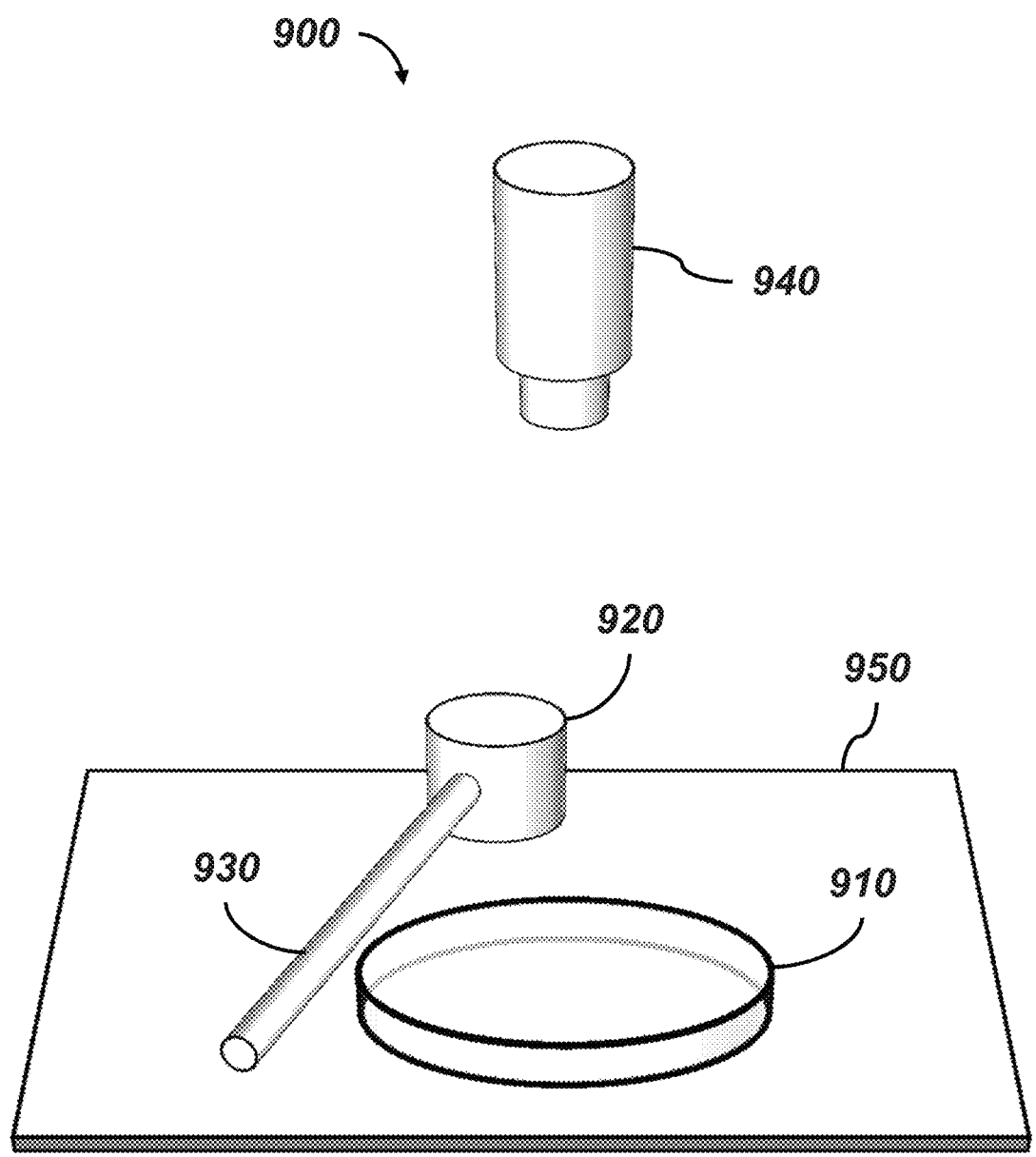
FIG. 9 is a diagrammatic illustration of an embodiment of an arrangement of components in a vibriosensation assay.

This assay is typically used to classify how animals react to mild water disturbances. Referring to FIG. 9, the assay arrangement (900) utilizes the fact that planarians in a test zone (910), such as a petri dish or well, can sense vibrations using ciliated neurons. Water disturbances in the test zone (910) can be created using a vortex shaker or vibrational plate or a motorized tapping device (which may include a servo (920) connected to a rod (930) positioned to tap the side of the test zone (910)). The assays may utilize a camera (940) and an LED panel (950).

In one example, vibration sensation experiments were conducted in a standard 100 mm petri dish. The dish was immobilized by inserting it in the corresponding lid, which was glued to a cold light LED panel and modified using a silicone paste to snugly hold the petri dish in place. The petri dish was filled with 25 ml of MS before 4-8 planarians were added to the dish using a transfer pipet. Control animals and experimental animals were assayed alternatingly. All conditions were assayed in triplicate, with a total of N=20 specimen each. To account for potential behavioral differences independent of the stimulus, no stimulus controls were performed for all conditions. The trials consisted of three 8-second free runs followed by 3 stimuli of 10 taps each. The taps were fully automated using a computer-controlled custom-tapping device. Recording was performed at 5 fps using a Basler A641f CCD camera and a custom MATLAB routine. Image analysis was performed in MATLAB to obtain COM motion and worm length over time. To account for size differences amongst planarians, the average gliding length for each animal was calculated and applied to further analysis. The behavior of each animal during each tapping series was then quantified as the contraction amplitude, which is the ratio of worm length at the maximum contraction to the average gliding length. The series of data for experimental or matching control groups was averaged and the experimental measurements were normalized to the control, which was set to 1.

Moving beyond descriptions of the individual assay stations themselves, certain embodiments of the method or system include evaluating whether an agent has an effect on a planarian's ability to integrate across multiple stimuli. While it is known that planaria can integrate across different sensory stimuli (Inoue et al., *Zoological Letters* 2015), how agent exposure affects that ability has not been tested. In certain embodiments, multiple stimuli, preferably two at a time, can be simultaneously used. For example, in one embodiment, thermotaxis may be combined with phototaxis whereby the different warm and cold regions could be exposed to different wavelength of light. In one embodiment, thermotaxis may be combined with chemotaxis and the stimuli could be combined with either opposing effects or with the same effects, i.e., preferred cold zone with adverse chemical or preferred cold zone with chemical attractant. This allows one to assay whether the response to the single stimulus is the same or enhanced when adding another stimulus of the same direction or whether a behavior can be suppressed if an opposing stimulus is added. Exposure to one or multiple agents may cause alterations to the planaria's capability of stimulus integration, causing a delay in response to the stimulus or modify or reverse the order of priority given to various stimuli compared to that in unexposed individuals. The same image analysis tools that are applied for quantifying the individual responses can be used to quantify the animals' behaviors in these multi-stimuli assays. In certain embodiments, the strength of one stimulus may be kept at a constant setting, whereas the strength of the other stimulus is being varied at fixed intervals to determine whether there was a certain threshold for eliciting a specific response. In a certain example embodiment, a planaria was exposed to a chemical attractant (food) when the second stimulus (noxious heat) was added. It was observed that the noxious stimulus overwrote the attractive stimulus and the planaria which initially moved toward the food source, retracted from the food source upon administration of the second stimulus. Image analysis was performed similar to the single stimulus assays described above, using a custom MATLAB script and COM tracking.

In some embodiments of the method or system, the effects of an agent across different assay readouts can be integrated to generate a phenotypic profile. This profile may provide an overview of the different morphological or behavioral changes induced by exposure to that agent. For most of the behavioral assays, changes in behavior can be quantified as either increased or decreased reactions, allowing for discrimination of neuroactivity vs neurotoxicity. Clustering techniques, for e.g. hierarchical clustering or principal component analysis, may be used to group agents with phenotypic profiles. Thus, phenotypic profiling of known agents can be used to classify new agents whose mechanism is not yet known.

Figure 7A:
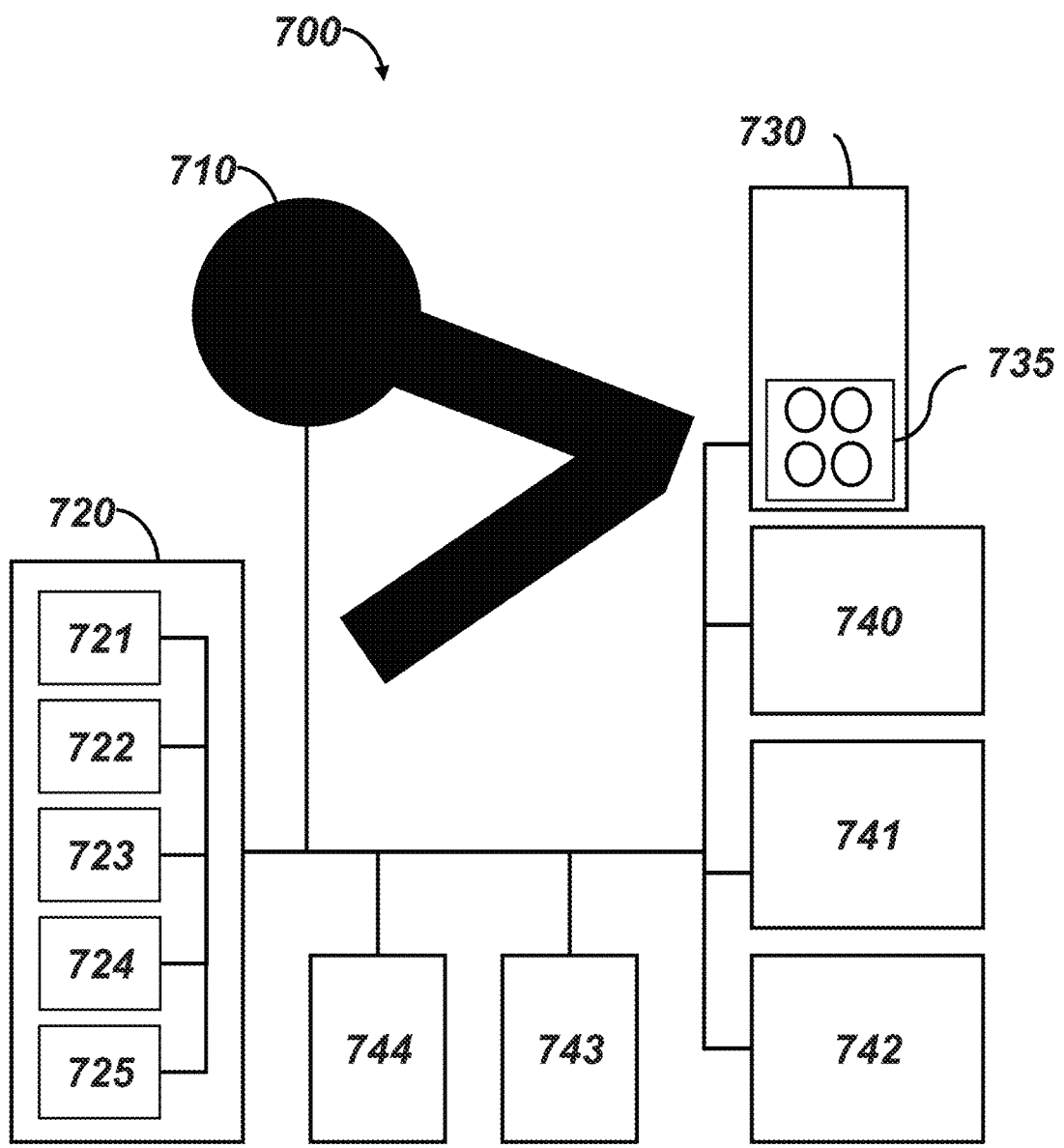
FIGS. 7A and 7B are diagrammatic illustrations of embodiments of the disclosed system.

Referring now to FIG. 7A, certain embodiments of a system (700) performing these methods utilizes a robotic arm (710), which may include but is not limited to 3- to 6-axis robotic arm plate handlers capable of moving plates (735) from one location to another, typically either from a storage location (730) to an assay station (740, 741, 742), or from one assay station to another.

The system shown in FIG. 7A uses one or more processors (721) and memory (722) in some sort of protective housing (720). This may include, for example, a desktop computer, and a remote server. The system also may include a database (723) and a communications interface (724) for, e.g., communicating and/or controlling the robotic arm (710), the storage apparatus (730), and/or the assay stations (740, 741, 742). The processor (721) and memory (722) may contain instructions for communicating and/or controlling any or all of the other components.

The processor (721) and memory (722) may also contain instructions that allow the processor to receive data from each camera. In some embodiments, each assay station has one or more cameras. In other embodiments, one or more cameras are automatically moved into position over each of the assay stations at an appropriate time.

The processor (721) and memory (722) may also need instructions that allow the processor to parse the data it receives from each camera. For example, the processor may need to parse a data/time stamp of a given image.

The processor (721) and memory (722) may also contain instructions that allow the evaluation of the data from each camera. As described above, these instructions may contain image processing and/or ML algorithms that allow the quantification of lethality, unstimulated behavior, locomotion, chemotaxis, phototaxis, thermotaxis, regeneration, scrunching, body morphology, general health, fission rates, generational studies, vibriosensation, and stickiness.

The processor (721) and memory (722) may also contain instructions that store the evaluations in the database (723). In some embodiments, the raw data is also stored. In some embodiments, only the data required to present a graph or image are stored. For example, in some embodiments, the processor may only need to store the date/time of a lethality assay, the number of "dead" planaria, and the number of "live" planaria.

In some embodiments, the processor (721) and memory (722) may also contain instructions that associates a unique identifier for the test zone or plate of test zones with a given evaluation. That unique identifier may be stored along with the evaluation.

The system (700) may also include a display (725). In such cases, the processor (721) and memory (722) may also contain instructions that displays the evaluations to a user, which may include but is not limited to displaying an image, displaying recorded images or video, displaying graphs, or displaying tables.

The system (700) may also include an automated guillotine (743) such as that shown in FIG. 3, or automated planarian loader (744) such as that shown in FIG. 2. The automated guillotine can be configured to decapitate at least one planarian, while the automated planarian loader can be configured to place at least a portion of a planarian in a well.

The system (700) may also include an assay station (740) that is configured to generate a mechanical disturbance within at least one well of the multi-well array. In certain embodiments, this includes a variable rpm vortex shaker that is customized for multi-well plates and computer-controlled system to always reset to a fixed starting position. In some embodiments, the plate shaking may be achieved using a vibrational table. In some embodiments, the fluid disturbance may be achieved using a fluid pulse at a fixed flow rate.

The system (700) may also include an assay station (741) that includes a plurality of Peltier devices. The Peltier devices are configured to generate a substantially equal temperature gradient within each well of the multi-well arrays, such that the coldest temperatures in each well are all within +/−4 degrees C., and preferably +/−2 degrees C. In some embodiments, the gradient in each well are all within +/−4 degrees C. per cm, preferably +/−3 degrees C. per cm, more preferably +/−2 degrees C. per cm, and still more preferably within +/−1 degree C. per cm. In certain embodiments, the gradients in each well are all between 1-3 degrees C. per cm. In preferred embodiments, the coldest temperature in the well is between 15 and 25 degrees C., and more preferably less than 20 degrees C.

The system (700) may also include an assay station (742) that includes a first light capable of irradiating a test zone at a first point in time with radiation having a first peak wavelength. In some embodiments, this may include a light in the blue wavelength range, which typically has a peak wavelength between 450 and 495 nm. The station may also include a second light capable of irradiating the test zone at a second point in time with radiation having a second peak wavelength. In some embodiments, this may include a light in the green wavelength range, which typically has a peak wavelength between 495 and 570 nm. In certain embodiments, the station may also include a third light capable of irradiating the test zone at a third point in time with radiation having a third peak wavelength. In some embodiments, this may include a light in the red wavelength range, which typically has a peak wavelength between 620 and 750 nm. In certain embodiments, the system may use the red light as "dark"—since the planarians are not sensitive to red light, and the system may generate pulses of the blue and/or green lights. In some embodiments, two or more lights may be shown simultaneously.

Figure 7B:
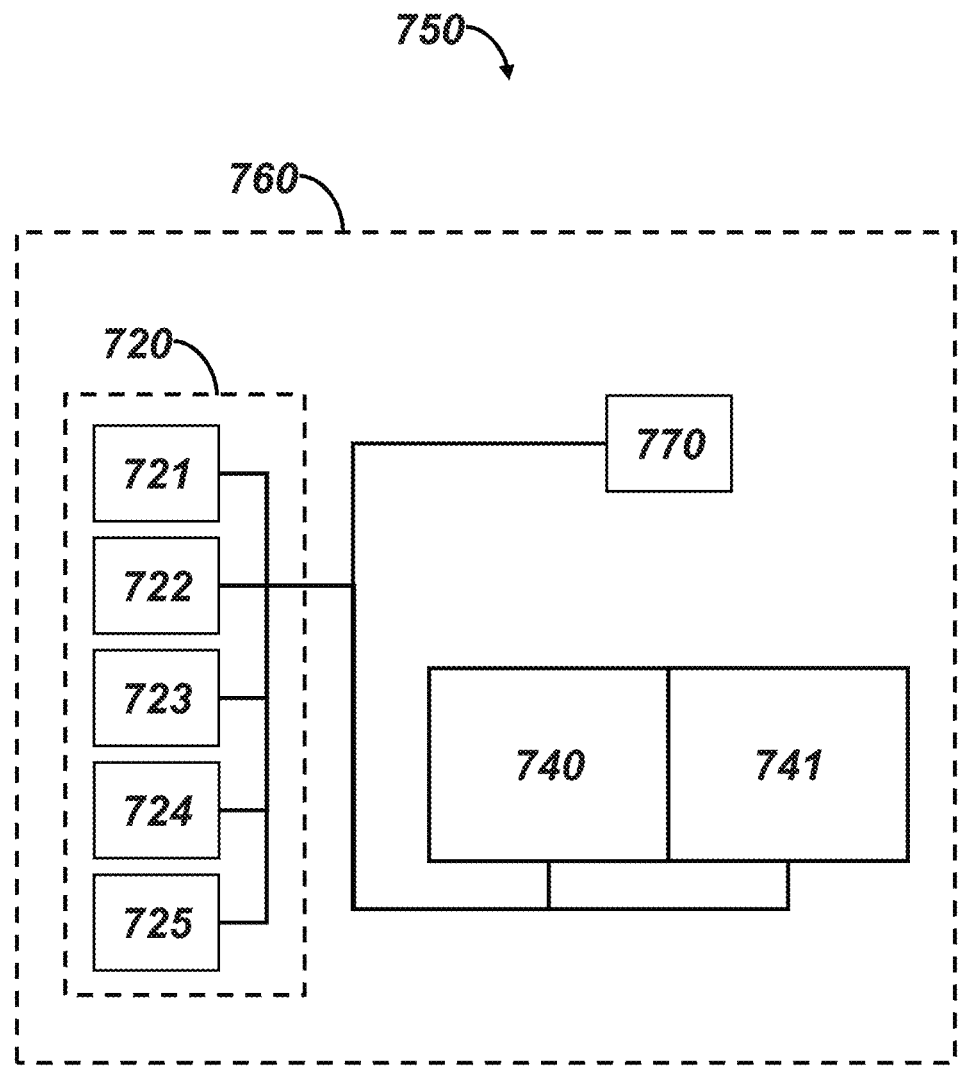

Referring now to FIG. 7B, in certain embodiments of the system (750), some or all of the assay stations (740, 741) mentioned may be contained within a protective housing or box (760). The protective housing or box (760) is intended to be portable. As such, the overall weight of the system (750) is preferably less than 20 pounds, and the housing or box (760) preferably has handholds, slots, or other means for enabling a person to readily transport the box. In certain embodiments, between 2 and 8 assay stations, preferably between 2 and 6 assay stations, more preferably between 2 and 4 assay stations, and still more preferably exactly 4 assay stations are contained in the protective housing. One or more cameras (770) may be positioned above the assay stations (740, 741). The system uses one or more processors (721) and memory (722), which may be a separate protective housing (720). In FIG. 7B, the processor (721), memory (722), database (723), communication interface (724), and display (725) within protective housing (720) are shown as also being within protective housing (760). However, in certain embodiments, those elements are external to protective housing (760), for example, attached to the outside of protective housing (760), or remotely located from protective housing (760) and only operably connected via, e.g., an ethernet or other wired connection. This may include, for example, an Arduino board which may also be connected to a desktop computer and/or a remote server. The processor (721) is provided instructions for controlling the assay stations (740, 741). The processor (721) and memory (722) may also contain instructions for communicating and/or controlling any or all of the other components.

Those skilled in the art will recognize or be able to ascertain using no more than routine experimentation many equivalents to the specific embodiments of the invention described herein. Such equivalents are intended to be encompassed by the following claims.

What is claimed is:

1. A high throughput method for analyzing effects of a plurality of agents on planaria, comprising:
   a. providing a plurality of test zones, each test zone having at least a portion of one planarian;
   b. exposing the planaria in each of the plurality of test zones to at least one agent;
   c. sealing the plurality of test zones to prevent transport in or out of each test zone;
   d. utilizing a crane, plate handler, or conveyor belt for moving the plurality of test zones to one of a plurality of assay stations, and between assay stations;
   e. exposing the plurality of test zones to a set of conditions;
   f. capturing an image or video of the at least a portion of one planarian in each test zone;
   g. evaluating whether the at least one agent has at least one effect on the at least a portion of one planarian in each test zone at the one of a plurality of assay stations; and
   h. repeating steps (d) through (g) until each test zone has been evaluated by each of the assay stations;
   wherein the method further comprises amputating at least one planarian into at least two fragments using an automated guillotine, the automated guillotine comprising a descending guillotine oriented perpendicular to a channel through which the at least one planarian is travelling.

2. The high throughput method according to claim 1, wherein each of the plurality of assay stations is:
   i. an assay station configured to quantify stickiness by having the assay station generate a mechanical disturbance within a test zone, capturing images or video of the test zone, and evaluating the captured images or video using computational image analysis to determine when the at least a portion of one planarian detaches from a surface;
   j. an assay station configured to quantify body morphology and overall health by capturing images or video of a test zone and evaluating the captured images or video using computational image analysis to score physical body characteristics;
   k. an assay station configured to quantify chemotaxis by capturing images or video of a test zone and evaluating the captured images or video using computational image analysis to score behavior of each of at least one portion of one planarian in each of the test zones;
   l. an assay station configured to quantify temperature sensing, including creating a temperature gradient, capturing images or video of the test zone, and evaluating the captured images or video using computational image analysis to score behavior;
   m. an assay station configured to quantify light detection by exposing each test zone with light at different times, capturing at least one image of the test zone when exposed to a first light having at least a first peak wavelength and at least one image of the test zone when exposed to a second light having a second peak wavelength, and evaluating the captured images using computational image analysis to score behavior in response to the first and second lights;
   n. an assay station configured to quantify viability or lethality by capturing images or video of a test zone and evaluating the captured images or video using computational image analysis to classify each of at least one portion of one planarian in each of the test zones as alive or dead;
   o. an assay station configured to quantify regeneration by capturing an image of a test zone and evaluating the captured image using computational image analysis to quantify regeneration dynamics;
   p. an assay station configured to quantify vibrio sensation by generating a disturbance within a test zone, capturing video of the test zone, and evaluating the captured video using computational image analysis to determine a contraction amplitude of at least one planarian; or
   q. an assay station configured to quantify unstimulated behavior/locomotion by capturing images or video of an unstimulated test zone and evaluating the captured images or video using computational image analysis to track at least one portion of one planarian over a period of between 30 seconds and 10 minutes.

3. The high throughput method according to claim 1, wherein images of each test zone are captured beginning 15 minutes after the at least a portion of one planarian is added to the test zone and capturing at least one image on at least one day from day 1 through day 30 after the at least a portion of one planarian is added to the test zone.

4. The high throughput method according to claim 1, wherein each of the plurality of test zones is a well in a multi-well array.

5. The high throughput method according to claim 4, wherein each multi-well array is marked with a unique identifying mark, where the unique identifying mark is an ID number or a 1-D or 2-D barcode.

6. The high throughput method according to claim 5, wherein the unique identifying mark and data from each evaluation are stored in a database, and wherein the unique identifying mark is scanned at each assay station.

7. The high throughput method according to claim 1, further comprising evaluating whether the at least one agent has at least one effect on the at least a portion of one planarian's ability to integrate across multiple stimuli.

8. The high throughput method according to claim 1, wherein the plurality of assay stations includes:
   r. an assay station configured to quantify stickiness by having the assay station generate a mechanical disturbance within a test zone, capturing images or video of the test zone, and evaluating the captured images or video using computational image analysis to determine when the at least a portion of one planarian detaches from a surface;
s. an assay station configured to quantify chemotaxis by capturing images or video of a test zone and evaluating the captured images or video using computational image analysis to score behavior of each of at least one portion of one planarian in each of the test zones;
t. an assay station configured to quantify regeneration by capturing an image of a test zone and evaluating the captured image using computational image analysis to quantify regeneration dynamics; and/or
u. an assay station configured to quantify vibrio sensation by generating a disturbance within a test zone, capturing video of the test zone, and evaluating the captured video using computational image analysis to determine a contraction amplitude of at least one planarian.

9. The method of claim 2, wherein each test zone is exposed to each of assay stations (i)-(q).

* * * * *